(12) United States Patent
Hayes

(10) Patent No.: US 9,333,159 B2
(45) Date of Patent: May 10, 2016

(54) TOPICAL DNA REPAIR COMPOSITION

(75) Inventor: Barbara F. Hayes, New York, NY (US)

(73) Assignee: PHOTOMEDEX, INC., Horsham, PA (US)

( * ) Notice: Subject to any disclaimer, the term of this patent is extended or adjusted under 35 U.S.C. 154(b) by 0 days.

(21) Appl. No.: 14/114,651

(22) PCT Filed: Apr. 26, 2012

(86) PCT No.: PCT/US2012/035124
§ 371 (c)(1),
(2), (4) Date: Aug. 4, 2014

(87) PCT Pub. No.: WO2012/149110
PCT Pub. Date: Nov. 1, 2012

(65) Prior Publication Data
US 2014/0335137 A1    Nov. 13, 2014

Related U.S. Application Data

(60) Provisional application No. 61/481,123, filed on Apr. 29, 2011.

(51) Int. Cl.
| | | |
|---|---|---|
| *A61K 36/00* | (2006.01) |
| *A61K 8/66* | (2006.01) |
| *A61K 36/31* | (2006.01) |
| *A61K 8/27* | (2006.01) |
| *A61K 8/29* | (2006.01) |
| *A61Q 17/04* | (2006.01) |
| *A61K 8/99* | (2006.01) |
| *A61K 8/14* | (2006.01) |
| *A61K 8/49* | (2006.01) |
| *A61Q 19/00* | (2006.01) |
| *A61K 8/97* | (2006.01) |
| *A61K 8/37* | (2006.01) |
| *A61Q 19/08* | (2006.01) |

(52) U.S. Cl.
CPC ... *A61K 8/66* (2013.01); *A61K 8/14* (2013.01); *A61K 8/27* (2013.01); *A61K 8/29* (2013.01); *A61K 8/37* (2013.01); *A61K 8/4946* (2013.01); *A61K 8/975* (2013.01); *A61K 8/99* (2013.01); *A61K 36/31* (2013.01); *A61Q 17/04* (2013.01); *A61Q 19/00* (2013.01); *A61Q 19/004* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2004/0057917 A1 | 3/2004 | Wolf et al. | |
| 2006/0002884 A1* | 1/2006 | Golz-Berner et al. | 424/74 |
| 2007/0207195 A1* | 9/2007 | Yarosh et al. | 424/450 |
| 2007/0254021 A1 | 11/2007 | Scimeca et al. | |
| 2009/0117060 A1 | 5/2009 | Golz-Berner et al. | |
| 2010/0291190 A1 | 11/2010 | Giampapa | |

FOREIGN PATENT DOCUMENTS

| | | |
|---|---|---|
| DE | 4244418 A1 * | 7/1993 |
| DE | 20316269 | 2/2005 |
| EP | 1634576 | 3/2006 |
| WO | 2008/002609 | 1/2008 |
| WO | 2009/023416 | 2/2009 |

OTHER PUBLICATIONS

Merck Manual Home Edition, Overview of Sunlight and Skin Damage, accessed on Jun. 26, 2015, pp. 1-3.*
Goihman-Yahr, Skin aging and photoaging: an outlook, Clinics in Dermatology 14: 153-160, 1996.*
Tyrrell, Solar UV damage and skin protection: the boosting of natural defences and healing by cosmeceuticals. Bulletin Technique Gattefosse (2013), 106, 72-81.*
Tanaka, Protecting skin photoaging by NF-kappaB inhibitor. Current drug metabolism, (Jun. 1, 2010) vol. 11, No. 5, pp. 431-435.*
Goh, The treatment of visible signs of senescence: the Asian experience. The British journal of dermatology, (Apr. 1990) vol. 122 Suppl 35, pp. 105-109.*
International Search Report, Australian Patent Office, Application No. PCT/US2012/035124, Jul. 27, 2012.
International Written Opinion, Australian Patent Office, Application No. PCT/US2012/035124, Jul. 27, 2012.
European Extended Search Report, European Patent Office, Co-pending European National Phase Application No. 12776676.4, Nov. 28, 2014.

* cited by examiner

*Primary Examiner* — Qiuwen Mi
(74) *Attorney, Agent, or Firm* — Gottlieb, Rackman & Reisman, PC

(57) ABSTRACT

Provided herein are topical compositions for repairing sun damaged skin and topical sunscreen compositions for both preventing and repairing sun damage.

5 Claims, 6 Drawing Sheets

Localized Pigmentation

Start

Week 4

4 WEEK RESULTS
>20% Reduction in localized Pigmentation

Pores

Start

Week 4

4 WEEK RESULTS
>50% Reduction in Pores

Texture

Start

Week 4

4 WEEK RESULTS
>40% Improvement in Texture

Under-Eye Circles
Comparative Analysis Pre vs Post Treatment

Left Eye
Placebo
Week 8

Right Eye
Treated
Week 8

TOPICAL DNA REPAIR COMPOSITION

RELATED APPLICATIONS

This application claims priority to U.S. Provisional Application No. 61/481,123, filed Apr. 29, 2011. Where permitted, this application is incorporated by reference in its entirety.

TECHNICAL FIELD

Embodiments provided herein relate generally to the fields of cosmetics and dermatology industries, and more specifically to compositions for repairing sun damage to the skin.

BACKGROUND

Exposure to ultraviolet (UV) radiation from sunlight can cause a variety of skin conditions including cosmetic defects such as discoloration, pore formation, age spots, spider veins, and rough texture, as well as serious diseases such as skin cancer. Sun exposure can also lead to the appearance of premature aging by causing the skin to lose its elasticity and form wrinkles.

Various topical creams, lotions, and ointments have been made in an attempt to address the negative effects of sun damage on the skin either by prevention or treatment. However, preventive topical compositions such as conventional sunscreens are inadequate because they typically wash or rub off, require frequent re-application, and are not properly or thoroughly applied. Nevertheless, even with proper application of common sunscreens, UV exposure and DNA damage can still occur despite a high sun protection factor (SPF). Similarly, conventional topical compositions for treating sun damaged skin are inadequate and fail to address the multiple complex cellular levels impacted by sun exposure. Such deficient conventional products are limited to addressing only a single cellular aspect of the complex cascade of cellular damage caused by sun exposure.

SUMMARY

In one embodiment, a topical composition for repairing sun damaged skin includes one or more plant, algae, or bacteria extracts; liposomes containing at least a portion of said one or more extracts; a peptone or synthesized peptide comprising a metal atom binding site; a metal atom bound to said metal binding site; and a topically suitable carrier. In another embodiment, a topical composition for repairing sun damaged skin includes one or more DNA repair enzyme-containing extracts; liposomes containing at least a portion of said one or more extracts; a peptide bound to a metal atom; and a topically suitable carrier. Without intending to be bound by theory, in such embodiments the user benefits from simultaneity of the independent, but mutually adjuvant and non-internecine, actions of the peptide or peptone and the enzyme.

In one aspect, the plant extract includes *Arabidopsis thaliana* extract, the algae extract includes *Anacystis nidulans* extract, and the bacteria extract includes *Micrococcus luteus* extract.

In various aspects of the aforementioned embodiments, the one or more extracts contain at least one DNA repair enzyme. In one aspect, the at least one DNA repair enzyme is selected from the group consisting of photolyase, UV endonuclease, and OGG1.

In a further aspect, the aforementioned embodiments include an *Arabidopsis thaliana* extract. In the same aspect, the *Arabidopsis thaliana* extract contains OGG1.

In an additional aspect, the aforementioned embodiments include a cyanobacteria extract derived from plankton. In the same aspect, the cyanobacteria is *Anacystis nidulans*. In the same aspect, the *Anacystis nidulans* extract contains photolyase.

In yet another aspect, the aforementioned embodiments include *Micrococcus luteus* extract. In the same aspect, the *Micrococcus luteus* extract contains UV endonuclease.

In various aspects of the aforementioned embodiments, the metal binding site comprises at least two amino acids selected from Arg, His, and Lys. In the same aspect, the peptide consists of 3 amino acids. Further in the same aspect, the 3 amino acids have the sequence Gly-His-Lys. In another aspect, the 3 amino acids have the sequence Ala-His-Lys.

In various aspects of the aforementioned embodiments, the metal atom is copper (II), cadmium (II), tin (II), cobalt (II), iron (II), or manganese (II). In the same aspect, the metal atom is copper (II).

In various aspects of the aforementioned embodiments, the liposomes comprise phospholipids, oleic acid, and cholesterol. In one aspect, the liposomes are about 200 nm in diameter.

In another embodiment, a topical composition for repairing sun damaged skin includes one or more DNA repair enzymes selected from the group consisting of photolyase from *Anacystis nidulans*, UV endonuclease from *Micrococcus luteus*, and OGG1 from *Arabidopsis thaliana*; liposomes containing said one or more DNA repair enzymes; a peptone or synthesized peptide comprising a metal atom binding site; a metal atom bound to said metal binding site; and a topically suitable carrier.

In one aspect, the one or more enzymes are recombinantly expressed. In the same aspect, the one or more recombinantly expressed enzymes are purified by chromatography.

In various aspects of the aforementioned embodiment, the metal binding site comprises at least two amino acids selected from Arg, His, and Lys.

In various aspects of the aforementioned embodiment, the metal binding site comprises at least two amino acids selected from Arg, His, and Lys. In the same aspect, the peptide consists of 3 amino acids. Further in the same aspect, the 3 amino acids have the sequence Gly-His-Lys. In another aspect, the 3 amino acids have the sequence Ala-His-Lys.

In various aspects of the aforementioned embodiment, the metal atom is copper (II), cadmium (II), tin (II), cobalt (II), iron (II), or manganese (II). In the same aspect, the metal atom is copper (II).

In various aspects of the aforementioned embodiment, the liposomes comprise phospholipids, oleic acid, and cholesterol. In one aspect, the liposomes are about 200 nm in diameter.

In an additional embodiment, a sunscreen composition for preventing and repairing sun damage to skin includes one or more algae or bacteria extracts; liposomes containing at least a portion of said one or more extracts; a mineral UV blocking agent; and a super antioxidant. In a further embodiment, a sunscreen composition for preventing and repairing sun damage to skin includes one or more DNA repair enzyme-containing extracts; liposomes containing at least a portion of said one or more extracts; a mineral UV blocking agent; and a super antioxidant.

In one aspect, the composition further includes a plant extract. In the same aspect, the plant is *Arabidopsis thaliana*.

In various aspects of the aforementioned embodiments, the one or more algae extracts includes *Anacystis nidulans* extract and the one or more bacteria extracts the one or more algae extracts includes *Micrococcus luteus* extract.

In various aspects of the aforementioned embodiments, the one or more extracts contain at least one DNA repair enzyme. In the same aspect, the at least one DNA repair enzyme is selected from the group consisting of photolyase, UV endonuclease, and OGG1.

In a further aspect of the aforementioned embodiments, the sunscreen composition includes an *Arabidopsis thaliana* extract. In the same aspect, the *Arabidopsis thaliana* extract contains OGG1.

In an additional aspect of the aforementioned embodiments, the sunscreen composition includes a cyanobacteria extract derived from plankton. In the same aspect, the cyanobacteria is *Anacystis nidulans*. Further in the same aspect, the *Anacystis nidulans* extract contains photolyase.

In a further aspect of the aforementioned embodiments, the sunscreen composition includes *Micrococcus luteus* extract. In the same aspect, the *Micrococcus luteus* extract contains UV endonuclease.

In various aspects of the aforementioned embodiments, the mineral UV blocking agent is a metal oxide compound. In the same aspect, the metal oxide compound is zinc oxide. Further in the same aspect, the metal oxide compound is titanium oxide. In some aspects, the zinc oxide or titanium oxide is micronized.

In various aspects of the aforementioned embodiments, the super antioxidant is ergothioneine.

In various aspects of the aforementioned embodiments, the topical sunscreen composition includes at least two or more algae or bacteria extracts.

In various aspects of the aforementioned embodiments, the topical sunscreen composition further includes a UV filter. In the same aspect, the UV filter is octisalate. Further in the same aspect, the octisalate is present in an amount of about 2.5% to about 3.0% w/w.

In another aspect, the UV filter is octinoxate. In the same aspect, octinoxate is present in an amount of about 6.5% to 7.5% w/w.

In various aspects of the aforementioned embodiments, zinc oxide is present in an amount of at least 7.50% w/w. In various aspects of the aforementioned embodiments, the titanium oxide is present in an amount of about 3.5% w/w. In various aspects of the aforementioned embodiments, the liposomes comprise phospholipids, oleic acid, and cholesterol. In the same aspect, the liposomes are about 200 nm in diameter.

In various aspects of the aforementioned embodiments, the topical sunscreen composition includes a *Anacystis nidulans* photolyase and *Micrococcus luteus* UV endonuclease In various aspects of the aforementioned embodiments, the topical sunscreen composition is capable of providing a sun protection factor (SPF) rating of at least 30. In the same aspect, the topical sunscreen composition is capable of providing a sun protection factor (SPF) rating of at least 43. Further in the same aspect, the composition is capable of providing a sun protection factor (SPF) rating of at least 45.

It will be appreciated that any of the foregoing embodiments or aspects thereof can be used in conjunction with one another.

DETAILED DESCRIPTION

Figure 1:
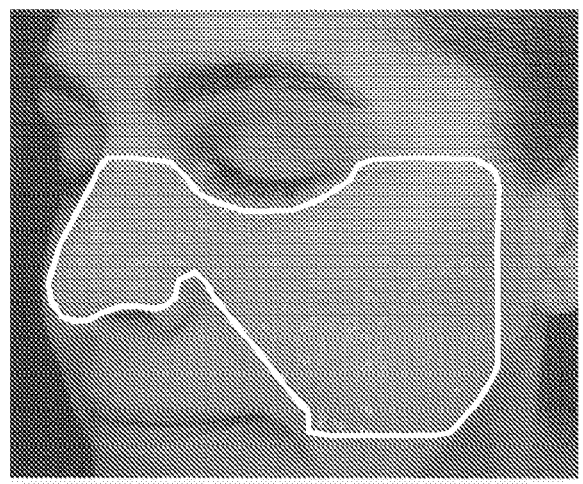
FIG. 1 is a panel of photographic images and a bar graph quantifying reduction in localized pigmentation of a human female subject given a treatment regimen including various topical compositions described herein.
Figure 1:
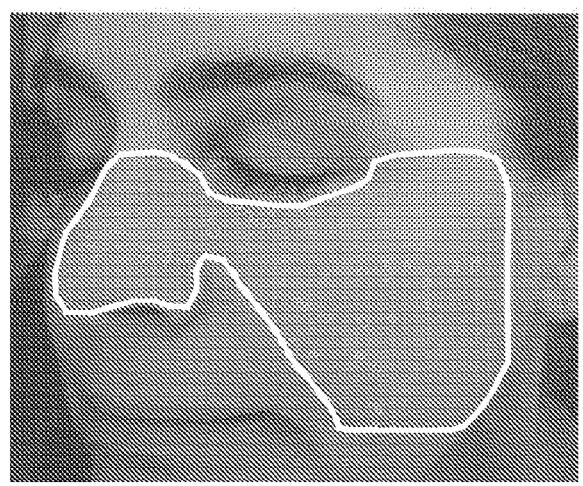
Figure 1:
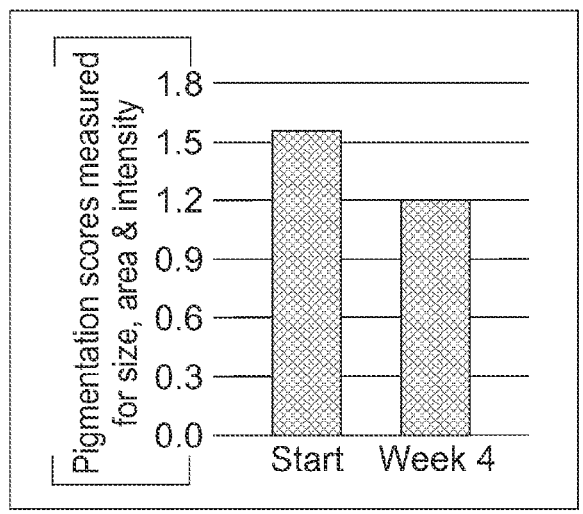

Several embodiments described herein relate to topical compositions for treating sun damaged skin that represent a multi-faceted approach in targeting a plurality of cellular aspects of skin damage caused by sunlight. Every day, even in cloud cover, ultraviolet (UV) radiation assaults exposed skin and causes DNA damage. DNA absorbs both UVA and UVB radiation and is understood to undergo a photochemical reaction that produces cyclobutane pyrimidine dimers and other photoproducts that impair cellular integrity. As a result of DNA damage, both direct to the DNA and indirect and collateral to other tissues and functions, early stages of damage manifest as skin texture and tone loss, wrinkle formation, and hyperpigmentation. As DNA damage accumulates, later stages of damage can present as actinic keratosis and skin cancer. Furthermore, UV radiation also breaks down collagen and extracellular matrix components, and impairs collagen neosynthesis and elastin functionality. By virtue of addressing the multiple cellular events of damage caused by the sun, several embodiments provided herein improve the appearance and health of the skin, which can be appreciated, for example, by visible reduction of wrinkles, pigmentation, discoloration, pores, and/or dark under-eye circles.

Various embodiments described herein relate to topical compositions that address these multiple cellular aspects of the complex cascade of cellular damage caused by sun exposure. Without being bound by theory, topical compositions of several embodiments described herein simultaneously repair genotoxic insults of sun exposure via the action of one or more DNA repair enzymes and facilitate repairing the extracellular matrix via the action of one or more metal peptide complexes. Without being bound by theory, various embodiments are drawn to independent repair mechanisms acting in concert to fix the pleiotropic array of damage caused by the sun at different cellular levels. In doing so, but without intending to be limited by theory, several embodiments provided herein can improve the symptoms of sun damage. For example, several embodiments provided herein can improve the appearance and health of the skin by promoting reduction of wrinkles, pigmentation, discoloration, pores, and/or dark under-eye circles.

Additionally, without intending to be limited by such a consideration, several embodiments provided herein drawn to independent repair mechanisms acting in concert are contemplated to provide better subject compliance, thereby leading to greater improvement at the cellular level and also at the level of overall skin appearance and health. Without intending to be bound by theory, it is contemplated that several embodiments described herein couple short-term and long-term benefits at the cellular level and overall skin appearance. Accordingly, several embodiments provided herein will benefit subjects who typically and preferentially comply with advised protocols for using compositions that provide short-term benefits over compositions that merely provide longer term benefits. The short-term benefits of the compositions provided herein encourage subject compliance by providing immediately recognizable benefits from the compositions provided herein, which high subject compliance results in an increased efficacy of the long-term beneficial effects of the compositions provided herein. By complying with the advised protocols due to the coupling of short-term and long-term benefits, various embodiments herein can take advantage of high subject compliance for short-term benefits whilst providing the long-term benefits that would ordinarily be forgone by subjects due to a failure by subjects to recognize only gradual, long-term improvement.

Additionally, several embodiments are drawn to topical compositions for both preventing and repairing sun damage to skin cells for maximum protection from harmful UV rays. Without being bound by theory, topical sunscreen compositions of various embodiments described herein not only prevent UV damage, but also simultaneously repair DNA damage that inevitably gets past the action of components that block and/or filter UV radiation. Various embodiments of sunscreen compositions prevent UV damage while repairing nascent DNA damage before mutagenic insults on the genome accumulate, require a more extensive repair, and present as actinic keratosis and skin cancer characteristic of later stages of unrepaired or incompletely repaired DNA damage.

Topical Compositions for Repairing Sun Damaged Skin

Described herein are topical compositions for repairing sun damaged skin. In several embodiments, a topical composition comprises: one or more plant, algae, or bacteria extracts; liposomes containing at least a portion of the one or more extracts; a peptide comprising a metal atom binding site; and a metal atom bound to the metal atom binding site of the peptide.

In various embodiments, the one or more plant, algae, or bacteria extracts preferably provide a source of at least one DNA repair enzyme. As used herein, the terms "plant," "algae," and "bacteria" do not have a strict taxonomical distinction and can include overlapping members due to the lack of a consensus uniform taxonomy system and varied colloquial use of these terms. For example, cyanobacteria (commonly referred to as blue-green algae) were historically considered to be "algae" but modernly are considered to be bacteria. As such, the terms "plant," "algae," and "bacteria" as used herein are meant to encompass overlapping members.

Additionally, the term "plankton" refers to any marine organism that inhabits bodies of water including but not limited to oceans, seas, lakes, rivers, and streams. Typically, but not necessarily, plankton are drifting organisms that flow with water current. Accordingly, plankton are conveniently referred to by their ecological niche rather than taxonomic classification and the term "plankton" as used herein can refer to organisms classifiable as animals, plants, algae, and/or bacteria without mutual exclusion.

As used herein, the term "DNA repair enzyme" refers to an enzyme that is able to repair DNA damage. Without being bound by theory, such DNA repair enzymes are often categorized by the type of DNA damage they repair.

The term "extract" refers to a composition derived from plant, algae, and/or bacteria. An extract can include a portion or the entirety of the plant, algae, and/or bacteria from which a composition is derived. Furthermore, extracts may take any physical form such as but not limited to liquids and powders. An extract can be derived from plant, algae, and/or bacteria by extraction techniques well known in the art.

Extracts

Various embodiments of topical compositions for repairing sun damaged skin can include at least one plant, algae, and/or bacteria extract(s). In several embodiments, the extract is derived from the plant species *Arabidopsis thaliana*. In several embodiments, the extract is derived from plankton which includes the algae species *Anacystis nidulans*. In several embodiments, the extract is derived from the bacteria species *Micrococcus luteus*.

In some embodiments, an extract from one or more plant, algae, and/or bacteria extract(s) provides a source of at least one DNA repair enzyme. For example, the extract can be derived from the plant species *Arabidopsis thaliana*, which provides a source of at least one DNA repair enzyme. In some embodiments, the plant extract contains the DNA repair enzyme 8-oxoguanine DNA glycosylase (OGG1). For example, the extract can be an extract from *Arabidopsis thaliana*, which contains the DNA repair enzyme OGG1. Without wishing to be bound by theory, it is believed that OGG1 repairs the oxidative 8-oxoguanine damages in both genomic and mitochondrial DNA.

The amount of plant extract in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of *Arabidopsis thaliana* extract is about 0.0015%, about 0.0025%, about 0.0035%, about 0.0045%, about 0.01%, about 0.05%, about 0.10%, about 0.15%, about 0.20%, about 0.25%, about 0.30%, about 0.40%, about 0.45%, about 0.50%, about 0.75%, or about 1.0% w/w. Methods of preparing plant extracts are known in the art and can be used in the embodiments described herein.

In several embodiments, the extract can be derived from plankton that includes the algae species *Anacystis nidulans*, which provides a source of at least one DNA repair enzyme. In some embodiments, the algae extract contains the DNA repair enzyme photolyase. For example, the plankton extract can be an extract including *Anacystis nidulans*, which contains the DNA repair enzyme photolyase. Without being bound by theory, it is believed that photolyase, through a process called "photoreactivation," repairs pyrimidine dimers that arise when a pair of thymine or cytosine bases on the same strand of DNA becomes covalently linked by UV irradiation.

The amount of plankton extract in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of plankton extract containing the algae species *Anacystis nidulans* is about 0.005%, about 0.01%, about 0.05%, about 0.10%, about 0.15%, about 0.20%, about 0.25%, about 0.30%, about 0.40%, about 0.45%, about 0.50%, about 0.75%, or about 1.0% w/w. Methods of preparing plankton extracts are known in the art and can be used in the embodiments described herein.

In various embodiments, topical compositions for repairing sun damaged skin can include at least one algae extract and at least one surfactant, examples of which are described below. It has been reported in the field that algae extract (e.g. plankton extract) contemplated for use with liposomes is incompatible with surfactants. However, several embodiments of topical compositions for repairing sun damaged skin provided herein contemplate a hitherto unrecognized compatibility among algae extract (e.g. plankton extract), liposomes, and one or more surfactants.

In some embodiments, an extract can be derived from the bacteria species *Micrococcus luteus*, which provides a source of at least one DNA repair enzyme. In some embodiments, the bacterial extract contains the DNA repair enzyme UV endonuclease. For example, the extract can be an extract from *Micrococcus luteus*, which contains the DNA repair enzyme UV endonuclease. Without wishing to be bound by theory, it is believed that UV endonuclease recognizes pyrimidine dimers caused by UV irradiation and initiates the repair process.

The amount of bacteria extract in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to about 0.55% w/w, about 0.25% to about 0.50% w/w, about 0.30% to about 0.45% w/w, or any range or amount in between the aforementioned ranges. In some embodiments, the amount of *Micrococcus luteus* extract is about 0.0015%, about 0.0025%, about 0.0035%, about 0.0045%, about 0.0090%, about 0.05%, about 0.10%, about 0.15%, about 0.20%, about 0.25%, about 0.30%, about 0.40%, about 0.45%, about 0.50%, about 0.75%, or about 1.0% w/w. Methods of preparing bacteria extracts are known in the art and can be used in the embodiments described herein.

In various embodiments, topical compositions for repairing sun damaged skin can include at least one bacteria extract and at least one surfactant, examples of which are described below. It has been reported in the field that bacteria extract (e.g. *Micrococcus luteus* extract) contemplated for use with liposomes is incompatible with surfactants. However, several embodiments of topical compositions for repairing sun damaged skin provided herein contemplate a hitherto unrecognized compatibility among bacteria extract (e.g. *Micrococcus luteus* extract), liposomes, and one or more surfactants.

DNA Repair Enzymes

The deterioration of the appearance and function of skin is often associated with skin damage caused by ultraviolet irradiation resulting from sun exposure. Without being bound by theory, UV rays from the sun cause DNA damage in skin cells at least in part by inducing formation of pyrimidine dimers, which can block both DNA transcription and replication and thereby contribute to the development of certain skin cancers. Addressing sun-induced DNA damage, various embodiments of topical compositions for repairing sun damaged skin can include one or more DNA repair enzymes, either present in a plant, algae, and/or bacteria extract, or in isolated or purified form. In certain embodiments, the one or more DNA repair enzymes can be recombinantly expressed by standard molecular cloning techniques and optionally purified by standard biochemical techniques known in the art.

Contemplated herein are any DNA repair enzymes known to those skilled in the art, including but not limited to UV endonuclease, endonuclease V, photolyase, and OGG1, which can be used in the compositions provided herein. Resources for determining those DNA repair enzymes known in the art including but not limited to UV endonuclease, endonuclease V, photolyase, and OGG1 are readily available and include, but are not limited to GenBank, SwissProt, EMBL, etc., the contents of which, as applied to UV endonucleases, endonuclease V, photolyase, and OGG1 are incorporated expressly herein in their entirety.

Accordingly, in several embodiments a topical composition comprises: one or more DNA repair enzymes; liposomes containing the one or more DNA repair enzymes; a peptide comprising a metal atom binding site; and a metal atom bound to the metal atom binding site of the peptide. In one aspect, the one or more DNA repair enzymes are selected from photolyase, UV endonuclease, and OGG1. In the same aspect, the one or more DNA repair enzymes are selected from *Anacystis nidulans* photolyase, *Micrococcus luteus* UV endonuclease, and *Arabidopsis thaliana* OGG1.

Liposomes

In several embodiments, one or more DNA repair enzyme(s), whether present as a component of an extract or in isolated or purified form, are contained in liposomes. As used herein, the term "liposome" means a vesicle composed of amphiphilic lipids arranged in a relatively spherical bilayer or bilayers.

Liposomes are unilamellar or multilamellar vesicles which have a membrane formed from a lipophilic material and an aqueous interior. The aqueous interior portion contains the composition to be delivered. Phospholipids used for liposome formation include, but are not limited to, natural phospholipids such as egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanolamine, diphosphatidyl glycerol. Liposome preparation is described, for example, in U.S. Pat. Nos. 7,208,174, 7,108,863, 5,192,549, 6,958,241, and in Ann. Rev. Biophys. Bioeng., 9, 467 (1980), "Liposomes" (Ed. by M. J. Ostro, Marcel Dekker, Inc.) the entire contents of which are incorporated herein by reference. In several embodiments, one or more DNA repair enzyme(s), whether present as a component of an extract or in isolated or purified form, are contained in multilamellar liposomes.

When phospholipids and many other amphipathic lipids are dispersed gently in an aqueous medium they swell, hydrate and spontaneously form multilamellar concentric bilayer vesicles with layers of aqueous media separating the lipid bilayers. These systems commonly are referred to as multilamellar liposomes or multilamellar vesicles (MLV) and usually have diameters of from 0.2 μm to 5 μm. Sonication of MLV results in the formation of small unilamellar vesicles (SUV) with diameters usually in the range of 20 to 100 nm, containing an aqueous solution in the core. Multivesicular liposomes (MVL) differ from multilamellar liposomes in the random, non-concentric arrangement of chambers within the liposome. Amphipathic lipids can form a variety of structures other than liposomes when dispersed in water, depending on the molar ratio of lipid to water, but at low ratios the liposome is the preferred structure.

The physical characteristics of liposomes generally depend on pH and ionic strength. They characteristically show low permeability to ionic and polar substances, but at certain temperatures can undergo a gel-liquid crystalline phase (or main phase) transition dependent upon the physical properties of the lipids used in their manufacture which markedly alters their permeability. The phase transition involves a change from a closely packed, ordered structure, known as the gel state, to a loosely packed, less-ordered structure, known as the liquid crystalline state.

Various types of lipids differing in chain length, saturation, and head group have been used in liposomal formulations for years, including the unilamellar, multilamellar, and multivesicular liposomes mentioned above.

There are at least three types of liposomes. The term "multivesicular liposomes (MVL)" generally refers to man-made, microscopic lipid vesicles comprising lipid membranes enclosing multiple non-concentric aqueous chambers. In contrast, "multilamellar liposomes or vesicles (MLV)" have multiple "onion-skin" concentric membranes, in between which are shell-like concentric aqueous compartments. Multilamellar liposomes and multivesicular liposomes characteristically have mean diameters in the micrometer range, usually from 0.5 to 25 µm. The term "unilamellar liposomes or vesicles (ULV)" generally refers to liposomal structures having a single aqueous chamber, usually with a mean diameter range from about 20 to 500 nm.

Multilamellar and unilamellar liposomes can be made by several relatively simple methods. A number of techniques for producing ULV and MLV are described in the art (for example in U.S. Pat. No. 4,522,803 to Lenk; U.S. Pat. No. 4,310,506 to Baldeschweiler; U.S. Pat. No. 4,235,871 to Papahadjopoulos; U.S. Pat. No. 4,224,179 to Schneider, U.S. Pat. No. 4,078,052 to Papahadjopoulos; U.S. Pat. No. 4,394,372 to Taylor U.S. Pat. No. 4,308,166 to Marchetti; U.S. Pat. No. 4,485,054 to Mezei; and U.S. Pat. No. 4,508,703 to Redziniak).

By contrast, production of multivesicular liposomes generally requires several process steps. Briefly, a common method for making MVL is as follows: The first step is making a "water-in-oil" emulsion by dissolving at least one amphipathic lipid and at least one neutral lipid in one or more volatile organic solvents for the lipid component, adding to the lipid component an immiscible first aqueous component and a biologically active substance to be encapsulated, and optionally adding, to either or both the lipid component and the first aqueous component, an acid or other excipient for modulating the release rate of the encapsulated biologically active substances from the MVL. The mixture is emulsified, and then mixed with a second-immiscible aqueous component to form a second emulsion. The second emulsion is mixed either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them (see Kim et al., Biochem. Biophys. Acta, 728:339-348, 1983). For a comprehensive review of various methods of ULV and MLV preparation, refer to Szoka, et al. Ann. Rev. Biophys. Bioeng. 9:465-508, 1980.

Making multivesicular liposomes can involve inclusion of at least one amphipathic lipid and one neutral lipid in the lipid component. The amphipathic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phosphatidylglycerols, phosphatidylserines, phosphatidylinositols, phosphatidic acids, etc. Examples of cationic amphipathic lipids are diacyl trimethylammonium-propane and ethyl phosphatidylcholine. Examples of neutral lipids include diglycerides, such as diolein, dipalmitolein, and mixed caprylincaprin diglycerides; triglycerides, such as triolein, tripalmitolein, trilinolein, tricaprylin, and trilaurin; vegetable oils, such as soybean oil; animal fats, such as lard and beef fat; squalene; tocopherol; and combinations thereof. Additionally, cholesterol or plant sterols can be used in making multivesicular liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

In several embodiments described herein, liposomes that contain one or more DNA repair enzymes, whether present as a component of an extract or in isolated or purified form, can be of various compositions. For example, the liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In various embodiments, liposomes can be composed of phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions can be formed from dimyristoyl phosphatidylglycerol, while anionic fusogenic liposomes can be formed from dioleoyl phosphatidylethanolamine (DOPE). Another type of liposomal composition can be formed from phosphatidylcholine (PC) such as, for example, soybean PC, and egg PC. Another type can be formed from mixtures of phospholipid and/or phosphatidylcholine and/or cholesterol.

Examples of phospholipids suitable for use in several embodiments include but are not limited to DOPC or DC18:1PC=1,2-dioleoyl-sn-glycero-3-phosphocholine; DLPC or DC12:0PC=1,2-dilauroyl-sn-glycero-3-phosphocholine; DMPC or DC14:0PC=1,2-dimyristoyl-sn-glycero-3-phosphocholine; DPPC or DC16:0PC=1,2-dipalmitoyl-sn-glycero-3-phosphocholine; DSPC or DC18:0PC=1,2-distearoyl-sn-glycero-3-phosphocholine; DAPC or DC20:0PC=1,2-diarachidoyl-sn-glycero-3-phosphocholine; DBPC or DC22:0PC=1,2-dibehenoyl-sn-glycero-3-phosphocholine; DC16:1PC=1,2-dipalmitoleoyl-sn-glycero-3-phosphocholine; DC20:1PC=1,2-dieicosenoyl-sn-glycero-3-phosphocholine DC22:1PC=1,2-dierucoyl-sn-glycero-3-phosphocholine; DPPG=1,2-dipalmitoyl-sn-glycero-3-phosphoglycerol; DOPG=1,2-dioleoyl-sn-glycero-3-phosphoglycerol.

Additional examples of phospholipids suitable for use in several embodiments provided herein include but are not limited to those listed in Table 1 below.

TABLE 1

| Abbreviation | CAS | Name | Type |
|---|---|---|---|
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . .) (Sodium Salt) | Phosphatidylglycerol |
| DLOPC | 998-06-1 | 1,2-Dilinoleoyl-sn-glycero-3-phosphocholine | Phosphatidylcholine |
| DLPA-NA | | 1,2-Dilauroyl-sn-glycero-3-phosphate (Sodium Salt) | Phosphatidic acid |
| DLPC | 18194-25-7 | 1,2-Dilauroyl-sn-glycero-3-phosphocholine | Phosphatidylcholine |
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . .) (Sodium Salt) | Phosphatidylglycerol |
| DLPG-NH4 | | 1,2-Dilauroyl-sn-glycero-3[Phospho-rac-(1-glycerol . . .) (Ammonium Salt) | Phosphatidylglycerol |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . .) (Sodium Salt) | Phosphatidylglycerol |
| DMPG-NH4 | | 1,2-Dimyristoyl-sn-glycero-3[Phospho-rac-(1-glycerol . . .) (Ammonium Salt) | Phosphatidylglycerol |
| DMPG-NH4/NA | | 1,2-Dimyristoyl-sn-glycero-3[Phospho-rac-(1-glycerol . . .) (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |
| DOPG-NA | 62700-69-0 | 1,2-Dioleoyl-sn-glycero-3[Phospho-rac-(1-glycerol . . .) (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol . . .) (Sodium Salt) | Phosphatidylglycerol |
| DPPG-NH4 | 73548-70-6 | 1,2-Dipalmitoyl-sn-glycero-3[Phospho-rac-(1-glycerol . . .) (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . .) (Sodium Salt) | Phosphatidylglycerol |

TABLE 1-continued

| Abbreviation | CAS | Name | Type |
|---|---|---|---|
| DSPG-NH4 | 108347-80-4 | 1,2-Distearoyl-sn-glycero-3[Phospho-rac-(1-glycerol . . .) (Ammonium Salt) | Phosphatidylglycerol |
| DSPS-NA | | 1,2-Distearoyl-sn-glycero-3-phosphoserine (Sodium Salt) | Phosphatidylserine |
| Egg Sphingomyelin | | | |
| empty Liposome | | | |
| EPC | | Egg-PC | Phosphatidylcholine |
| HEPC | | Hydrogenated Egg PC | Phosphatidylcholine |
| HSPC | | High purity Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |
| Milk Sphingomyelin | | 1-Myristoyl-2-palmitoyl-sn-glycero 3-phosphocholine | Phosphatidylcholine |
| MPPC | | | |
| MSPC | | 1-Myristoyl-2-stearoyl-sn-glycero-3-phosphocholine | Phosphatidylcholine |
| PMPC | | 1-Palmitoyl-2-myristoyl-sn-glycero-3-phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol) . . .] (Sodium Salt) | Phosphatidylglycerol |
| PSPC | | 1-Palmitoyl-2-stearoyl-sn-glycero-3-phosphocholine | Phosphatidylcholine |
| SMPC | | 1-Stearoyl-2-myristoyl-sn-glycero-3-phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholine |

Furthermore, liposomes of the present embodiments can be of various sizes. For example, the diameter of a liposome in various embodiments can be about 300 nm, about 295 nm, about 290 nm, about 285 nm, about 280 nm, about 275 nm, about 270 nm, about 265 nm, about 260 nm, about 255 nm, about 250 nm, about 245 nm, about 240 nm, about 235 nm, about 230 nm, about 225 nm, about 220 nm, about 215 nm, about 210 nm, about 205 nm, about 200 nm, about 195 nm, about 190 nm, about 185 nm, about 180 nm, about 175 nm, about 170 nm, about 165 nm, about 160 nm, about 155 nm, about 150 nm, about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, or about 5 nm. In some embodiments, one or more DNA repair enzyme(s), whether present as a component of an extract or in isolated or purified form, are contained in liposomes that have a diameter of about 200 nm.

Various embodiments include pH sensitive liposomes. Without being bound by theory, it is believed that liposomes which are stable at neutral pH but release their contents at acidic pH can be used to deliver enzymes into the lysozymes of the cytoplasm, whereupon the contents are released. Since many DNA repair enzymes like the T4 endonuclease V are relatively stable at low pH, this method allows efficient delivery of active enzymes into cells.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized.

Examples of these charged molecules include but are not limited to oleic acid and cholesteryl hemisuccinate, which are negatively charged at neutral pH but become neutralized at pH 5. The effect of combining these together in a lipid bilayer is that at pH 9 all molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

By way of example and not limitation, pH sensitive liposomes can be produced by combining phosphatidylethanolamine and cholesteryl hemisuccinate (CHEMS) which destabilizes the liposome at a pH of about less than 4.5. Additionally, inclusion of oleic acid with phosphatidylethanolamine also destabilizes the lipid bilayer at a pH of about less than 6.5, and imparts a net negative charge to the liposome at neutral pH.

Liposomes composed of a mixture of phosphatidylcholine and phosphatidylethanolamine are more pH sensitive than those composed of phosphatidylethanolamine alone. In several embodiments, liposomes comprise phospholipids, oleic acid, and cholesterol.

The liposomes of several embodiments described herein can be prepared by combining a phospholipid component with an aqueous component containing the one or more DNA repair enzyme(s), whether present as a component of an extract or in isolated or purified form, under conditions which will result in vesicle formation. The phospholipid concentration should be adequate to form lamellar structures and the aqueous component should be compatible with stability of the DNA repair enzyme(s).

Phospholipids and aqueous components can be combined to form vesicles, for example, by drying the phospholipids onto glass and then dispersing them in the aqueous component; injecting phospholipids dissolved in a vaporizing or non-vaporizing organic solvent into the aqueous component which has previously been heated; and dissolving phospholipids in the aqueous phase with detergents and then removing the detergent by dialysis. The concentration of extract(s) or DNA repair enzyme(s) in the aqueous component can be increased by lyophilizing the extract(s) or DNA repair enzyme(s) onto dried phospholipids and then rehydrating the mixture with a reduced volume of aqueous buffer. Also, methods of producing liposomes in a microfluidizer and adjusting the shear pressure as a means to adjust liposome size are well known in the art.

The amount of liposomes in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of liposomes is about 0.0015%, about 0.0025%, about 0.0035%, about 0.0045%, about 0.01%, about 0.05%, about 0.10%, about 0.15%, about 0.20%, about 0.25%, about 0.30%, about 0.40%, about 0.45%, about 0.50%, about 0.75%, or about 1.0% w/w.

Metal Binding Peptides

Aged and sun damaged skin appears dry and wrinkly with diminished elasticity. However, DNA damage caused by sun exposure is only one aspect of a cascade of UV insult to the skin. Additionally, visible manifestations of damaged skin involves inadequately slow repair of the damaged underlying extracellular matrix (ECM). Dry, wrinkly, and loose skin involves a loss in elasticity at the cellular and tissue level; decreases in collagen, a gelatinous protein which gives strength and flexibility to connective tissues; and decreases in hydroxyproline, a proline-derived amino acid present in collagen.

Copper binding peptides have been shown to promote new blood vessel growth, enhance expression of growth factors, activate matrix metalloproteases, and stimulate formation of new collagen, elastin, and glycosaminoglycan components of tissue to accelerate repair of the underlying ECM of skin. However, it is contemplated herein that in some embodiments copper can be safely and effectively introduced into cells to provide healthful effects.

Addressing the multiple aspects of skin damage at the cellular and tissue levels, various embodiments drawn to compositions for repairing sun damaged skin not only address the DNA damage aspect of ultraviolet insult on skin cells, but also address the complex repair biology of the ECM. Accordingly, in several embodiments, compositions for repairing sun damaged skin include a "metal binding peptide," which refers to a peptide having a metal atom binding site for complexing with a metal to promote the health of the ECM.

In several embodiments, the metal binding peptide includes at least two amino acids selected from arginine (R), histidine (H), and lysine (K) (whether as D- or L-amino acids). Such metal binding peptides can be complexed or bound to a variety of metal atoms including but not limited to copper (II), cadmium (II), tin (II), cobalt (II), iron (II), manganese (II), zinc (II), indium (III), and tin (IV).

In certain embodiments, the metal binding peptide consists of 3 amino acids and includes, in any order, histidine, lysine, and any other amino acid. In some embodiments, the metal binding peptide consists of the sequence N terminus-glycine-histidine-lysine-C terminus or N terminus-alanine-histidine-lysine-C terminus. In various embodiments, the metal complexed or bound to the metal binding peptide is copper (II).

Solid Phase Synthesis

Metal binding peptides can be prepared by standard solid-phase peptide synthesis (SPPS) protocols, and optionally incorporate synthetic or non-naturally occurring amino acids and peptide backbone modifications. The standard methods include exclusive solid phase synthesis, partial solid phase synthesis methods, fragment condensation, classical solution synthesis, and even by recombinant DNA technology. See, for example, Merrifield, 1963 *J Am Chem Soc* 85:2149, incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO-BEADS SX-1 by BioRad Laboratories, Richmond, Calif., and the preparation of the hydroxymethyl resin is described by Bodonszky, et al. 1966 *Chem Ind (London)* 38:1597. The benzhydrylamine (BHA) resin has been described by Pietta and Marshall, 1970 *Chem Commn* 650, and is commercially available from Beckman Instruments, Inc., Palo Alto, Calif., in the hydrochloride form.

Thus, compounds can be prepared by coupling an alpha-amino protected amino acid to the chloromethylated resin with the aid of, for example, cesium bicarbonate catalyst, according to the method described by Gisin, 1973 *Helv Chim Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (for example, formyl, trifluoroacetyl, acetyl), aromatic urethane type protecting groups (for example benzyloxycarboyl (Cbz) and substituted Cbz), aliphatic urethane protecting groups (for example, t-butyloxycarbonyl (Boc), isopropyloxycarbonyl, cyclohexyloxycarbonyl) and alkyl type protecting groups (for example, benzyl, triphenylmethyl). The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z—Br—Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by J. M. Stewart and J. D. Young, 1984 *Solid Phase Peptide Syntheses* 2nd Ed., Pierce Chemical Company.

Synthetic or Non-naturally Occurring Amino Acids

Synthetic or non-naturally occurring amino acids refer to amino acids which do not naturally occur in vivo but which, nevertheless, can be incorporated into the peptide structures described herein. Examples of synthetic amino acids are the D-α-amino acids of naturally occurring L-α-amino acid as well as non-naturally occurring D- and L-α-amino acids represented by the formula $H_2NCHR^5COOH$ where $R^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5) -alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —$C(O)R^2$ where $R^2$ is selected from the group consisting of hydrogen, hydroxy, lower alkyl, lower alkoxy, and —$NR^3R^4$ where $R^3$ and $R^4$ are independently selected from the group consisting of hydrogen and lower alkyl, (g) —$S(O)_n$—$R^6$ where n is an integer from 1 to 2 and $R^6$ is lower alkyl and with the proviso that $R^5$ does not define a side chain of a naturally occurring amino acid.

Other synthetic amino acids include amino acids wherein the amino group is separated from the carboxyl group by more than one carbon atom such as β-alanine, γ-aminobutyric acid, and the like.

Additional synthetic amino acids include, by way of example, the D-amino acids of naturally occurring L-amino acids, L-(1-naphthyl)-alanine, L-(2-naphthyl)-alanine, L-cyclohexylalanine, L-2-aminoisobutyric acid, the sulfoxide and sulfone derivatives of methionine (i.e., HOOC—($H_2$NCH)$CH_2CH_2$—$S(O)_n$—$R^6$) where n and $R^6$ are as defined above as well as the lower alkoxy derivative of methionine (i.e., HOOC—($H_2$NCH)$CH_2CH_2$—$OR^6$ where $R^6$ is as defined above).

These procedures can also be used to synthesize peptides in which amino acids other than the 20 naturally occurring, genetically encoded amino acids are substituted at one, two, or more positions of any of the compounds of various embodiments. For instance, naphthylalanine can be substituted for tryptophan, facilitating synthesis. Other synthetic amino acids that can be substituted into the peptides of the some embodiments include L-hydroxypropyl, L-3,4-dihydroxy-phenylalanyl, d amino acids such as L-d-hydroxylysyl and D-d-methylalanyl, L-α-methylalanyl, β amino acids, and isoquinolyl. D amino acids and non-naturally occurring synthetic amino acids can also be incorporated into the peptides of various embodiments (see, for example, Roberts, et al. 1983 *Unusual Amino/Acids in Peptide Synthesis* 5:341-449).

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (for example, morpholino), oxazolyl, piperazinyl (for example, 1-piperazinyl), piperidyl (for example, 1-piperidyl, piperidino), pyranyl, pyrazinyl, pyrazolidinyl, pyrazolinyl, pyrazolyl, pyridazinyl, pyridyl, pyrimidinyl, pyrrolidinyl (for example, 1-pyrrolidinyl), pyrrolinyl, pyrrolyl, thiadiazolyl, thiazolyl, thienyl, thiomorpholinyl (for example, thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides of various embodiments by phosphorylation (see, for example, W. Bannwarth, et al. 1996 *Biorganic and Medicinal Chemistry Letters* 6:2141-2146), and other methods for making peptide derivatives of the compounds of various embodiments are described in Hruby, et al. 1990 *Biochem J* 268:249-262. Thus, the peptide compounds of various embodiments also serve as a basis to prepare peptidomimetics with similar biological activity.

Terminal Modifications

Those of skill in the art recognize that a variety of techniques are available for constructing peptidomimetics with the same or similar desired biological activity as the corresponding peptide compound but with more favorable activity than the peptide with respect to solubility, stability, and susceptibility to hydrolysis and proteolysis. See, for example, Morgan, et al. 1989 Ann Rep Med Chem 24:243-252. The following describes methods for preparing peptidomimetics modified at the N-terminal amino group, the C-terminal carboxyl group, and/or changing one or more of the amido linkages in the peptide to a non-amido linkage. It is understood that two or more such modifications can be coupled in one peptidomimetic structure (for example, modification at the C-terminal carboxyl group and inclusion of a —CH2- carbamate linkage between two amino acids in the peptide).

1). N-Terminal Modifications

The peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —NHCH3 or —NH(CH3)2), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (See, for example, Murray, et al. 1995 Burger's Medicinal Chemistry and Drug Discovery 5th ed., Vol. 1, Manfred E. Wolf, ed., John Wiley and Sons, Inc.) Specifically, the N-terminal amino group can then be reacted as follows:

(a) to form an amide group of the formula RC(O)NH— where R is as defined above by reaction with an acid halide [for example, RC(O)Cl or symmetric anhydride. Typically, the reaction can be conducted by contacting about equimolar or excess amounts (for example, about 5 equivalents) of an acid halide to the peptide in an inert diluent (for example, dichloromethane) preferably containing an excess (for example, about 10 equivalents) of a tertiary amine, such as diisopropylethylamine, to scavenge the acid generated during reaction. Reaction conditions are otherwise conventional (for example, room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (for example, about 5 equivalents) can be employed and the amino group is converted to the succinimide by methods well known in the art including the use of an excess (for example, ten equivalents) of a tertiary amine such as diisopropylethylamine in a suitable inert diluent (for example, dichloromethane). See, for example, Wollenberg, et al., U.S. Pat. No. 4,612,132 which is incorporated herein by reference in its entirety. It is understood that the succinic group can be substituted with, for example, C2-C6 alkyl or —SR substituents which are prepared in a conventional manner to provide for substituted succinimide at the N-terminus of the peptide. Such alkyl substituents are prepared by reaction of a lower olefin (C2-C6) with maleic anhydride in the manner described by Wollenberg, et al., supra and —SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ—Cl (i.e., benzyloxycarbonyl chloride) or a substituted CBZ—Cl in a suitable inert diluent (for example, dichloromethane) preferably containing a tertiary amine to scavenge the acid generated during the reaction;

(d) to form a sulfonamide group by reaction with an equivalent amount or an excess (for example, 5 equivalents) of R—S(O)2Cl in a suitable inert diluent (dichloromethane) to convert the terminal amine into a sulfonamide where R is as defined above. Preferably, the inert diluent contains excess tertiary amine (for example, ten equivalents) such as diisopropylethylamine, to scavenge the acid generated during reaction. Reaction conditions are otherwise conventional (for example, room temperature for 30 minutes);

(e) to form a carbamate group by reaction with an equivalent amount or an excess (for example, 5 equivalents) of R—OC(O)Cl or R—OC(O)OC6H4-p-NO2 in a suitable inert diluent (for example, dichloromethane) to convert the terminal amine into a carbamate where R is as defined above. Preferably, the inert diluent contains an excess (for example, about 10 equivalents) of a tertiary amine, such as diisopropylethylamine, to scavenge any acid generated during reaction. Reaction conditions are otherwise conventional (for example, room temperature for 30 minutes); and (f) to form a urea group by reaction with an equivalent amount or an excess (for example, 5 equivalents) of R—N=C=O in a suitable inert diluent (for example, dichloromethane) to convert the terminal amine into a urea (i.e., RNHC(O)NH—) group where R is as defined above. Preferably, the inert diluent contains an excess (for example, about 10 equivalents) of a tertiary amine, such as diisopropylethylamine. Reaction conditions are otherwise conventional (for example, room temperature for about 30 minutes).

2). C-Terminal Modifications

In preparing peptidomimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, for example, methanol. Side chain protecting groups are then removed in the usual fashion by treatment with hydrogen fluoride to obtain the desired ester.

In preparing peptidomimetics wherein the C-terminal carboxyl group is replaced by the amide —C(O)NR3R4, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH2). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O) NRR1 where R and R1 are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH2Cl2), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of various embodiments include amide, amide lower alkyl, amide di(lower alkyl), lower alkoxy, hydroxy, and carboxy, and the lower ester derivatives thereof, and the pharmaceutically acceptable salts thereof.

Backbone Modifications

Other methods for making peptide derivatives are described in Hruby, et al. 1990 *Biochem J* 268(2):249-262, incorporated herein by reference. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan, et al. 1989 *Ann Rep Med Chem* 24:243-252, incorporated herein by reference. These techniques include replacing the peptide backbone with a backbone composed of phosphonates, amidates, carbamates, sulfonamides, secondary amines, and N-methylamino acids.

Peptidomimetics wherein one or more of the peptidyl linkages [—C(O)NH—] have been replaced by such linkages as a —CH$_2$-carbamate linkage, a phosphonate linkage, a —CH$_2$-sulfonamide linkage, a urea linkage, a secondary amine (—CH$_2$NH—) linkage, and an alkylated peptidyl linkage [—C(O)NR$^6$— where R$^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —CH$_2$-carbamate linkage (—CH$_2$OC(O)NR—), then the carboxyl (—COOH) group of a suitably protected amino acid is first reduced to the —CH$_2$OH group which is then converted by conventional methods to a —OC(O)Cl functionality or a para-nitrocarbonate —OC(O)O—C$_6$H$_4$-p-NO$_2$ functionality. Reaction of either of such functional groups with the free amine or an alkylated amine on the N-terminus of the partially fabricated peptide found on the solid support leads to the formation of a —CH$_2$OC(O)NR— linkage. For a more detailed description of the formation of such —CH$_2$-carbamate linkages, see Cho, et al. 1993 *Science* 261:1303-1305.

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a —CH$_2$-sulfonamide linkage can be achieved by reducing the carboxyl (—COOH) group of a suitably protected amino acid to the —CH$_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH2-S(O)$_2$Cl functional group which replaces the carboxyl group of the otherwise suitably protected amino acid. Use of this suitably protected amino acid analogue in peptide synthesis provides for inclusion of a —CH$_2$S(O)$_2$NR— linkage, which replaces the amido linkage in the peptide thereby providing a peptidomimetic. For a more complete description on the conversion of the carboxyl group of the amino acid to a —CH$_2$S(O)$_2$Cl group, see, for example, Weinstein, B., 1983 *Chemistry & Biochemistry of Amino Acids, Peptides and Proteins* Vol. 7, pp. 267-357, Marcel Dekker, Inc., New York, which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —CH$_2$NH— linkage replaces the amido linkage in the peptide can be prepared by employing, for example, a suitably protected dipeptide analogue wherein the carbonyl bond of the amido linkage has been reduced to a CH$_2$ group by conventional methods. For example, in the case of diglycine, reduction of the amide to the amine will yield after deprotection H$_2$NCH$_2$CH$_2$NHCH$_2$COOH which is then used in N-protected form in the next coupling reaction. The preparation of such analogues by reduction of the carbonyl group of the amido linkage in the dipeptide is well known in the art (see, for example, M. W. Remington 1994 *Meth Mol Bio* 35:241-247).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One example of a tertiary amine is diisopropylethylamine which is typically employed in about 10-fold excess. The reaction results in incorporation into the peptidomimetic of an amino acid analogue having a non-peptidyl linkage. Such substitution can be repeated as desired such that from zero to all of the amido bonds in the peptide have been replaced by non-amido bonds.

In addition to the derivatives described above, other chemical modifications may be made to alter the biological activity of the derivatives of the metal binding peptides. For instance, in embodiments including a metal binding peptide comprising the sequence glycine-histidine-lysine (GHK), the glycine may be replaced by a variety of other small amino acids, including alanine, serine and valine. Further, the copper (II) binding affinity of the peptide could be increased by addition of an N-terminal amino acid such as glycine to convert glycyl-L-histidyl-L-lysine to glycyl-L-glycyl-L-histidyl-L-lysine. In addition, glycine could be added to a derivative as described above to create the corresponding tetrapeptide.

In various embodiments, the metal peptide complex derivatives of GHK have the general formula:

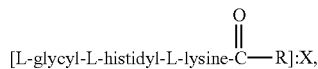

wherein X is a metal ion selected from the group consisting of copper (II), cadmium (II), cobalt (II), tin (II), iron (II) and manganese (II); and R is selected from the group consisting of an —NH$_2$ moiety, alkyl moieties containing from 1 to 18 carbon atoms, aryl moieties containing from 6 to 12 atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)n-L-tryptophan where n=1-4.

In various embodiments, the metal peptide complex derivatives of lysine-histidine-glycine (LHG) have the general formula:

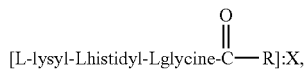

wherein X is a metal ion selected from the group consisting of copper (II), cadmium (II), cobalt (II), tin (II), iron (II) and manganese (II); and R is selected from the group consisting of an —NH$_2$ moiety, alkyl moieties containing from 1 to 18 carbon atoms, aryl moieties containing from 6 to 12 carbon atoms, alkoxy moieties containing from 1 to 18 carbon atoms, aryloxy moieties containing from 6 to 12 carbon atoms, alkylamino moieties containing from 1 to 18 carbon atoms, or where R is L-prolyl-L-valyl-L-phenylalanyl-L-valine, L-valyl-L-phenylalanyl-L-valine, L-tryptophan, or (glycyl)$_n$-L-tryptophan where n=1-4. One may utilize a ratio of GHK, KHG or derivative thereof to metal ion of 1:1, 2:1 or less. In some embodiments, a ratio of 0.5-0.9 metal atoms per GHK, KHG or derivative thereof is employed. As mentioned above, suitable metal ions include copper (II), cadmium (II), cobalt (II), tin (II), iron (II), manganese (II), and the like. In one embodiment, the pharmaceutical preparations described herein may be administered intradermally in the area to be treated, along with a suitable vehicle, in a concentration of approximately 100-500 micrograms of the metal-peptide composition per 0.1 ml of vehicle. Suitable vehicles in this regard include saline, sterile water, and the like.

Recombinant Expression and Peptone Digests

Alternatively, metal binding peptides can be recombinantly expressed in bacteria or other expression hosts according to known molecular biology techniques. Yet as another alternative, metal binding peptides can be prepared from hydrolytic or enzymatic protein digests, called peptones. Peptones are generally comprised of intermediate polypeptide products and mixtures of small peptides, formed in partial hydrolysis of proteins. Metal binding proteins can be generated from digests of soybean protein, casein, collagen, elastin, meat products (e.g., PRIMATONE), such as beef, liver, silk protein and so forth. By peptone digest is meant that the protein is degraded by enzymatic or hydrolytic (such as partial digestion with hydrochloric acid) digestion according to well known procedures.

Formation of Metal Peptide Complexes

In various embodiments of topical compositions for repairing sun damage, metal binding proteins and metal atoms are bound and are referred to as "metal peptide complex." Metal binding peptides can be bound to a variety of metal atoms including but not limited to copper (II), cadmium (II), tin (II), cobalt (II), iron (II), manganese (II), indium (III), and tin (IV). In several embodiments, the metal binding protein is a tripeptide having the amino acid sequence N terminus-glycine-histidine-lysine-C terminus and the metal atom bound to the tripeptide is copper (II), which together can be referred to as a "copper peptide complex."

To produce metal peptide complexes of various embodiments, the metal binding peptides are complexed with one or more ionic transition metals, such as copper, indium, tin, zinc or the salts thereof, such as sulfate, acetate, phosphate, etc. As an example, a synthetic metal binding peptide, recombinantly expressed metal binding peptide, or peptone digest yielding metal binding peptide can be dissolved in warm water (about 40° C.) at a concentration of about 5 to 50% (weight/volume), then mixed with an aqueous solution of a metal salt (e.g., copper (II) chloride) at a salt concentration of about 10 to 50% (w/v), more preferably about 20% (w/v). The volume of metal salt solution added is that amount needed to induce a copious precipitate in the solution, after the pH is adjusted to between about pH 6 to pH 7 to induce maximum formation of precipitate. Without being bound by theory, the term "complexed" refers to the peptides and metal ions forming electrostatic bonds.

Isolation and purification of metal peptide complexes can then be accomplished by any suitable separation or purification procedure such as, for example, filtration, extraction, centrifugation, crystallization, or a combination of these procedures. In an alternative method of preparation, metal binding peptides and metal atoms are directly combined in warm water (about 40°-60° C.) at concentrations which are the final concentrations desired for the formulation to be applied to the host. The pH of the mixture is adjusted (with sodium hydroxide or the like) to a pH between 6.0 and 7.0, and other aqueous components, as desired, are added, followed by blending in of carriers, smootheners, etc. for preparing a final formulation. This method avoids the necessity of a centrifugation step while producing formulations at the desired metal peptide complex final concentration.

In several embodiments, metal binding peptides can be synthesized by solution phase chemistry methods known in the art in which protected amino acids are added stepwise from the carboxy-terminus to generate the desired peptide. The resulting peptide can then be complexed to metal at the desired molar ratio of peptide to metal by dissolving the peptide in water, followed by addition of a suitable metal-salt (e.g. copper choloride) and adjusting the pH to greater than 4.0.

In various embodiments, aqueous solutions of peptide copper complexes can be prepared by methods that are well known to one skilled in the art. For example, an amount of dried peptide copper complex, suitable for a desired concentration, can be dissolved in water with mixing and gentle heating. As another example, a solution of the desired peptide can be prepared, followed by the addition of a copper salt in the desired molar ratio to yield the desired solution of the peptide copper complex. Non-limiting examples of copper salts that may be used include cupric chloride and cupric acetate. Aqueous solutions of peptide copper complexes can be neutralized with NaOH. In several embodiments, the ratio of peptide to copper can be 2 peptide to 1 copper, or 1 peptide to 1 copper.

The amount of metal peptide complex in various embodiments of topical compositions for repairing sun damaged skin can range from about 0.01% to about 5.0% w/w, about 0.10% to about 0.5% w/w, or about 0.20% to about 0.4% w/w, or any range or amount in between the aforementioned ranges. In some embodiments, the amount of metal peptide complex can be about 0.10%, about 0.20%, about 0.30%, about 0.40%, or about 0.50% w/w, or any amount in between the aforementioned amounts.

Accordingly, in several embodiments, a topical composition comprises: one or more plant, algae, or bacteria extracts; liposomes containing at least a portion of the one or more extracts; a peptide comprising a metal atom binding site; and a metal atom bound to the metal atom binding site of the peptide. In some aspects of the aforementioned embodiments, the one or more extracts is selected from *Arabidopsis thaliana*, *Anacystis nidulans*, and *Micrococcus luteus*, which in further aspects of the embodiments can provide a source of one or more DNA repair enzymes selected from OGG1, photolyase, and UV endonuclease. In such aspects, the peptide comprises a metal atom binding site which can comprise or consist of the amino acid sequence GHK, KHG, AHK, or KHA bound to copper.

Furthermore, in several embodiments a topical composition comprises: one or more DNA repair enzymes; liposomes containing the one or more DNA repair enzymes; a peptide comprising a metal atom binding site; and a metal atom bound to the metal atom binding site of the peptide. In some aspects, the one or more DNA repair enzymes are selected from photolyase, UV endonuclease, and OGG1. In the same aspect, the one or more DNA repair enzymes are selected from *Anacystis nidulans* photolyase, *Micrococcus luteus* UV endonuclease, and *Arabidopsis thaliana* OGG1. In any of these embodiments and aspects thereof, the peptide comprises a metal atom binding site which can comprise or consist of the amino acid sequence GHK, KHG, AHK, or KHA bound to copper.

Topical Compositions for Both Preventing and Repairing Sun Damage to Skin Cells

UVA rays are believed to account for up to 95 percent of the UV radiation reaching the Earth's surface. UVA rays are less intense than UVB rays, but are more prevalent and present with equal intensity during all daylight hours throughout the year and even penetrate clouds and glass. It is believed that UVA rays penetrate the skin more deeply than UVB and play a major role in photoaging and recently it has been appreciated that UVA rays cause significant damage in areas of the epidermis where most skin cancers occur. By contrast, UVB rays are thought to be responsible for sunburn and damage the skin's more superficial epidermal layers. Nonetheless, it is believed that UVB is involved in the development of skin cancer and contributes to tanning and photoaging. UVB intensity varies by season, location, and time of day, but UVB rays can burn and damage skin year-round, especially on reflective surfaces such as snow or ice, which reportedly can reflect up to 80% of the rays such that the skin is hit by the rays twice.

UV rays can damage skin at multiple cellular levels. Without being bound by theory, UV rays can damage DNA and trigger a cascade of cellular responses such as delaying activation of p53 protein, a tumor suppressor, which affects whether cells repair DNA damage, undergo programmed cell death process known as apoptosis, or undergo cell cycle arrest. UV rays can also cause mitochondrial distress as a result of oxidative damage, which can interfere with the initiation of apoptotic pathways that otherwise help prevent damaged cells from progressing to malignancy.

Currently available sunscreens provide inadequate protection from the sun's harmful DNA damaging UV rays because they only attempt to absorb or reflect UV rays, albeit incompletely, while ignoring the DNA damage that still occurs. Although conventional sunscreens may provide some protection from the harmful effects of UV exposure by reducing the amount of UV radiation which penetrates the outer epidermis, the stratum corneum, from reaching the underlying layers of living dermis, DNA damage cannot be fully prevented even with high sun protection factor (SPF) products.

Without being bound by theory, topical sunscreen compositions of various embodiments described herein not only prevent UV damage, but also simultaneously repair DNA damage that inevitably gets past the action of components that block and/or filter UV radiation. Various embodiments of sunscreen compositions prevent UV damage while repairing nascent DNA damage before mutagenic insults on the genome accumulate, require a more extensive repair, and present as actinic keratosis and skin cancer characteristic of later stages of unrepaired or incompletely repaired DNA damage. It is contemplated that topical sunscreen compositions provided herein are useful before, during, and after sun exposure and provide continuous correction at the DNA level while preventing and inhibiting new photodamage.

Topical compositions for both preventing and repairing sun damage to skin cells are described herein. Several embodiments of such compositions are drawn to sunscreens comprising: one or more plant, algae, or bacteria extracts; liposomes containing at least a portion of the one or more extracts; a mineral UV blocking agent; and a super antioxidant. Additional aspects of the aforementioned embodiments can further include UV filters, vitamins, colorants, fragrances, moisturizing agents, etc. described herein. Other embodiments comprise: one or more DNA repair enzymes, liposomes containing the one or more DNA repair enzymes, and micronized zinc oxide or micronized titanium dioxide. Such other embodiments can further include UV filters, antioxidants, vitamins, colorants, fragrances, moisturizing agents, etc. described herein.

Examples of a mineral UV blocking agent include but are not limited to metal oxides such as zinc oxide and titanium oxide. Without being bound by theory, mineral UV blocking agents act by physically blocking UV rays. For example, zinc oxide is recognized as a physical blocking agent for broad spectrum UVA-1, UVA-2, and UVB protection. Titanium oxide is recognized as a physical blocking agent for UVA-2 and UVB. The term "UV filter" generally refers to an agent that is considered to absorb, screen, reflect, and/or filter UV rays. The term "super antioxidant" generally refers to an agent having a potent antioxidant property. Without being bound by theory, a super antioxidant can refer to an agent having a quantitatively potent antioxidant property according to the Oxygen Radical Absorbance Capacity (ORAC) score, which is the USDA developed and accepted scientific measure of antioxidant potency for naturally occurring sources and extracts.

Extracts

Various embodiments of topical compositions for repairing sun damaged skin can include at least one plant, algae, and/or bacteria extract(s). In several embodiments, the extract is derived from the plant species *Arabidopsis thaliana*. In several embodiments, the extract is derived from plankton which includes the algae species *Anacystis nidulans*. In several embodiments, the extract is derived from the bacteria species *Micrococcus luteus*.

In some embodiments, an extract from one or more plant, algae, and/or bacteria extract(s) provides a source of at least one DNA repair enzyme. For example, the extract can be derived from the plant species *Arabidopsis thaliana*, which provides a source of at least one DNA repair enzyme. In some embodiments, the plant extract contains the DNA repair enzyme 8-oxoguanine DNA glycosylase (OGG1). For example, the extract can be an extract from *Arabidopsis thaliana*, which contains the DNA repair enzyme OGG1. Without wishing to be bound by theory, it is believed that OGG1 repairs the oxidative 8-oxoguanine damages in both genomic and mitochondrial DNA.

The amount of plant extract in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of *Arabidopsis thaliana* extract is about 0.0015%, about 0.0025%, about 0.0035%, about 0.0045%, about 0.01%, about 0.05%, about 0.10%, about 0.15%, about 0.20%, about 0.25%, about 0.30%, about 0.40%, about 0.45%, about 0.50%, about 0.75%, or about 1.0% w/w. Methods of preparing plant extracts are known in the art and can be used in the embodiments described herein.

In several embodiments, the extract can be derived from plankton that includes the algae species *Anacystis nidulans*, which provides a source of at least one DNA repair enzyme. In some embodiments, the algae extract contains the DNA repair enzyme photolyase. For example, the plankton extract can be an extract including *Anacystis nidulans*, which contains the DNA repair enzyme photolyase. Without being bound by theory, it is believed that photolyase, through a process called "photoreactivation," repairs pyrimidine dimers that arise when a pair of thymine or cytosine bases on the same strand of DNA becomes covalently linked by UV irradiation.

The amount of plankton extract in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of plankton extract containing the algae species *Anacystis nidulans* is about 0.005%, about 0.01%, about 0.05%, about 0.10%, about 0.15%, about 0.20%, about 0.25%, about 0.30%, about 0.40%, about 0.45%, about 0.50%, about 0.75%, or about 1.0% w/w. Methods of preparing plankton extracts are known in the art and can be used in the embodiments described herein.

In various embodiments, topical compositions for repairing sun damaged skin can include at least one algae extract and at least one surfactant, examples of which are described below. It has been reported in the field that algae extract (e.g. plankton extract) contemplated for use with liposomes is incompatible with surfactants. However, several embodiments of topical compositions for repairing sun damaged skin provided herein contemplate a hitherto unrecognized compatibility among algae extract (e.g. plankton extract), liposomes, and one or more surfactants.

In some embodiments, an extract can be derived from the bacteria species *Micrococcus luteus*, which provides a source of at least one DNA repair enzyme. In some embodiments, the bacterial extract contains the DNA repair enzyme UV endonuclease. For example, the extract can be an extract from *Micrococcus luteus*, which contains the DNA repair enzyme UV endonuclease. Without wishing to be bound by theory, it is believed that UV endonuclease recognizes pyrimidine dimers caused by UV irradiation and initiates the repair process.

The amount of bacteria extract in various embodiments of topical compositions for repairing sun damaged skin can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of *Micrococcus luteus* extract is about 0.0015%, about 0.0025%, about 0.0035%, about 0.0045%, about 0.0090%, about 0.05%, about 0.10%, about 0.15%, about 0.20%, about 0.25%, about 0.30%, about 0.40%, about 0.45%, about 0.50%, about 0.75%, or about 1.0% w/w. Methods of preparing bacteria extracts are known in the art and can be used in the embodiments described herein.

In various embodiments, topical compositions for repairing sun damaged skin can include at least one bacteria extract and at least one surfactant, examples of which are described below. It has been reported in the field that bacteria extract (e.g. *Micrococcus luteus* extract) contemplated for use with liposomes is incompatible with surfactants. However, several embodiments of topical compositions for repairing sun damaged skin provided herein contemplate a hitherto unrecognized compatibility among bacteria extract (e.g. *Micrococcus luteus* extract), liposomes, and one or more surfactants.

DNA Repair Enzymes

The deterioration of the appearance and function of skin is often associated with skin damage caused by ultraviolet irradiation resulting from sun exposure. Without being bound by theory, UV rays from the sun cause DNA damage in skin cells at least in part by inducing formation of pyrimidine dimers, which can block both DNA transcription and replication and thereby contribute to the development of certain skin cancers.

Addressing sun-induced DNA damage, various embodiments of topical compositions for repairing sun damaged skin can include one or more DNA repair enzymes, either present in a plant, algae, and/or bacteria extract, or in isolated or purified form. In certain embodiments, the one or more DNA repair enzymes can be recombinantly expressed by standard molecular cloning techniques and optionally purified by standard biochemical techniques known in the art.

Contemplated herein are any DNA repair enzymes known to those skilled in the art, including but not limited to UV endonuclease, endonuclease V, photolyase, and OGG1, which can be used in the compositions provided herein. Resources for determining those DNA repair enzymes known in the art including but not limited to UV endonuclease, endonuclease V, photolyase, and OGG1 are readily available and include, but are not limited to GenBank, SwissProt, EMBL, etc., the contents of which, as applied to UV endonucleases, endonuclease V, photolyase, and OGG1 are incorporated expressly herein in their entirety.

Accordingly, in several embodiments a topical composition comprises: one or more DNA repair enzymes; liposomes containing the one or more DNA repair enzymes; a peptide comprising a metal atom binding site; and a metal atom bound to the metal atom binding site of the peptide. In one aspect, the one or more DNA repair enzymes are selected from photolyase, UV endonuclease, and OGG1. In the same aspect, the one or more DNA repair enzymes are selected from *Anacystis nidulans* photolyase, *Micrococcus luteus* UV endonuclease, and *Arabidopsis thaliana* OGG1.

Liposomes

In several embodiments, one or more DNA repair enzyme(s), whether present as a component of an extract or in isolated or purified form, are contained in liposomes. Examples of liposomes that can be used in topical sunscreen embodiments are described above in detail with respect to topical compositions for repairing sun damaged skin.

The amount of liposomes in various embodiments of topical sunscreen compositions can range from about 0.001% to 10.0% w/w, about 0.002% to 5.0% w/w, about 0.003% to 3.0% w/w, about 0.004% to 2.0% w/w, about 0.005 to about 1.5% w/w, about 0.01% to about 1.0% w/w, about 0.02% to about 0.90% w/w, about 0.05% to about 0.80% w/w, about 0.10% to about 0.70% w/w, about 0.15% to about 0.60% w/w, about 0.20% to 0.55% w/w, about 0.25% to about 0.50% w/w, about 0.30% to about 0.45% w/w, or any range or amount in between the aforementioned ranges. In some embodiments, the amount of liposomes is about 0.01%, about 0.05%, about 0.10%, about 0.20%, about 0.50%, about 1.0%, about 2.0%, or about 5.0% w/w.

Mineral UV Blocking Agents

In several embodiments, topical sunscreen compositions can include one or more mineral UV blocking agents. Examples of mineral UV blocking agents include but are not limited to the class of agents referred to as metal oxides, such as zinc oxide and titanium oxide. In some embodiments, topical sunscreen compositions include micronized zinc oxide or micronized titanium oxide.

The amount of mineral UV blocking agents in various embodiments can each or collectively be about 1.0% to about 25.0% w/w, about 5% to about 10% w/w, or about 7.0% to about 8.0% w/w, or any number or range in between the aforementioned ranges. In some embodiments, the amount of micronized zinc oxide can be at least about 3.0%, about 3.5%, about 4.0%, about 4.5%, about 5.0%, about 5.5%, about 6.0%, about 6.5%, about 7.0%, about 7.5%, about 8.0%, about 8.5%, or about 9.0% w/w. In some embodiments, the amount of micronized titanium oxide can be at least about 1.0%, about 1.5%, about 2.0%, about 2.5%, about 3.0%, about 3.5%, about 4.0%, about 4.5%, or about 5.0% w/w.

UV Filters

Any of the topical sunscreen compositions for both preventing and repairing sun damage described herein can further include UV filters. Suitable organic UV filters for use in various embodiments can be selected from the group consisting of butyl methoxydibenzoylmethane (avobenzone), benzophenone-3 (oxybenzone), 4-methylbenzylidene camphor (enzacamene), benzophenone-4 (sulisobenzone), bis-ethylhexyloxyphenol methoxyphenyl triazine (bemotrizinol), diethylamino hydroxybenzoyl hexyl benzoate, diethylhexyl butamido triazone, disodium phenyl dibenzimidazole tetrasulfonate, drometrizole trisiloxane, ethylhexyl dimethyl PABA (padimate O), ethylhexyl methoxycinnamate (octinoxate), ethylhexyl salicylate (octisalate), ethylhexyl triazone, homosalate, isoamyl p-methoxycinnamate (amiloxate), isopropyl methoxycinnamate, menthyl anthranilate (meradimate), methylene bis-benzotriazolyl tetramethylbutylphenol (bisoctrizole), octocrylene, PABA (aminobenzoic acid), phenylbenzimidazole sulfonic acid (ensulizole), terephthalylidene dicamphor sulfonic acid, and mixtures thereof.

Octinoxate and/or octisalate are present in various embodiments of topical sunscreen compositions for both preventing and repairing sun damage.

The amount of any UV filter in various embodiments of topical compositions for both preventing and repairing sun damage can each or collectively range from about 1.0% to about 20.0% w/w, about 2.0% to about 10.0% w/w, about 3.0% to 8.0% w/w, or about 4.0% to 7.0% w/w, or any number or range in between the aforementioned ranges. In some embodiments, the amount of octinoxate can be at least about 6.0%, about 6.5%, about 7.0%, about 7.5%, about 8.0%, about 8.5%, or about 9.0% w/w. In some embodiments, the amount of octisalate can be at least about 1.0%, about 1.5%, about 2.0%, about 2.5%, about 3.0%, about 3.5%, about 4.0%, about 4.5%, or about 5.0% w/w.

FDA Sunscreen Monograph

Several embodiments of topical sunscreen compositions for both preventing and repairing sun damage include one or more components listed in the FDA Sunscreen Monograph (Table 2) at any amount up to the examples of upper maximum concentrations indicated in the Monograph. It will be understood that the upper maximum concentrations indicated in the Monograph are examples only and accordingly embodiments provided herein are not limited to such examples.

TABLE 2

| UV-filter | Other names | Example Upper Maximum concentration |
|---|---|---|
| p-Aminobenzoic acid | PABA | 15% (5% EC-will be banned from sale to consumers from 8 Oct. 2009) |
| Padimate O | OD-PABA, octyldimethyl-PABA, σ-PABA | 8% (EC, USA, AUS) 10% (JP) (Not currently supported in EU and may be delisted) |
| Phenylbenzimidazole sulfonic acid | Ensulizole, Eusolex 232, PBSA, Parsol HS | 4% (US, AUS) 8% (EC) 3% (JP) |
| Cinoxate | 2-Ethoxyethyl p-methoxycinnamate | 3% (US) 6% (AUS) |
| Dioxybenzone | Benzophenone-8 | 3% |
| Oxybenzone | Benzophenone-3, Eusolex 4360, Escalol 567 | 6% (US) 10% (AUS, EU) 5% (JP) |

TABLE 2-continued

| UV-filter | Other names | Example Upper Maximum concentration |
|---|---|---|
| Homosalate | Homomethyl salicylate, HMS | 10% (EC, JP) 15% (US, AUS) |
| Menthyl anthranilate | Meradimate | 5% |
| Octocrylene | Eusolex OCR, 2-cyano-3,3diphenyl acrylic acid, 2-ethylhexylester | 10% |
| Octyl methoxycinnamate | Octinoxate, EMC, OMC, Ethylmethoxy-cinnamate, Escalol 557, 2-ethylhexyl-paramethoxycinnamate, Parsol MCX | 7.5% (US) 10% (EC, AUS) 20% (JP) |
| Octyl salicylate | Octisalate, 2-Ethylhexyl salicylate, Escalol 587, | 5% (EC, USA, AUS) 10% (JP) |
| Sulisobenzone | 2-Hydroxy-4-Methoxybenzophenone-5-sulfonic acid, 3-benzoyl-4-hydroxy-6-methoxybenzenesulfonic acid, Benzophenone-4, Escalol 577 | 5% (EC) 10% (US, AUS, JP) |
| Trolamine salicylate | Triethanolamine salicylate | 12% |
| Avobenzone | 1-(4-methoxyphenyl)-3-(4-tert-butyl phenyl)propane-1,3-dione, Butyl methoxy dibenzoylmethane, BMDBM, Parsol 1789, Eusolex 9020 | 3% (US) 5% (EC, AUS) 10% (JP) |
| Ecamsule | Mexoryl SX, Terephthalylidene Dicamphor Sulfonic Acid | 10% |
| Titanium dioxide | CI77891 | 25% (No limit Japan) |
| Zinc oxide | | 25% (US) 20% (AUS) (EC-25% provided particle size >100 nm) (Japan, No Limit) |

European Union Approved Sunscreen Ingredients

Several embodiments of topical sunscreen compositions for both preventing and repairing sun damage include one or more components approved for use in the European Union (EU) (Table 3) at any amount up to the examples of upper maximum concentrations indicated. It will be understood that the upper maximum concentrations indicated in Table 3 are examples only and accordingly embodiments provided herein are not limited to such examples.

Sun Protection Factor (SPF)

The topical sunscreen compositions for both preventing and repairing sun damage described herein can be formulated to achieve various SPF ratings. The topical sunscreen compositions in some embodiments are intended to provide a sun protection factor (SPF) rating of at least 2, with additional preferable embodiments having a sun protection factor of at least 5, in other embodiments at least 10, in other embodiments at least 15, in other embodiments at least 20, in other embodiments at least 25, in other embodiments at least 30, in

TABLE 3

| UV-filter | Other names | Example Upper Maximum concentration | Permitted in |
|---|---|---|---|
| 4-Methylbenzylidene camphor | Enzacamene, Parsol 5000, Eusolex 6300, MBC | 4% | EC, AUS |
| Tinosorb M | Bisoctrizole, Methylene Bis-Benzotriazolyl Tetramethylbutylphenol, MBBT | 10% | EC, AUS, JP |
| Tinosorb S | Bis-ethylhexyloxyphenol methoxyphenol triazine, Bemotrizinol, BEMT, anisotriazine | 10% (EC, AUS) 3% (JP) | EC, AUS, JP |
| Neo Heliopan AP | Bisdisulizole Disodium, Disodium phenyl dibenzimidazole tetrasulfonate, bisimidazylate, DPDT | 10% | EC, AUS |
| Mexoryl XL | Drometrizole Trisiloxane | 15% | EC, AUS |
| Benzophenone-9 | Uvinul DS 49, CAS 3121-60-6, Sodium Dihydroxy Dimethoxy Disulfobenzophenone[63] | 10% | JP |
| Uvinul T 150 | Octyl triazone, ethylhexyl triazone, EHT | 5% (EC, AUS) 3% (JP) | EC, AUS |
| Uvinul A Plus | Diethylamino Hydroxybenzoyl Hexyl Benzoate | 10% (EC, JP) | EC, JP |
| Uvasorb HEB | Iscotrizinol, Diethylhexyl butamido triazone, DBT | 10% (EC) 5% (JP) | EC, JP |
| Parsol SLX | Dimethico-diethylbenzalmalonate, Polysilicone-15 | 10% | EC, AUS, JP |
| Isopentenyl-4-methoxycinnamate | Isoamyl p-Methoxycinnamate, IMC, Neo Heliopan E1000, Amiloxate | 10% | EC, AUS | other embodiments at least 35, in other embodiments at least 40, in other embodiments at least 45, in other embodiments at least 50, in other embodiments at least 55, in other embodiments at least 60, in other embodiments at least 65, in other embodiments at least 70, in other embodiments at least 75, in other embodiments at least 80, in other embodiments at least 85, in other embodiments at least 90, in other embodiments at least 95, and in other embodiments at least 100.

Embodiments of the topical sunscreen compositions for both preventing and repairing sun damage described herein can also provide U.S. FDA UV-A "star ratings" of at least one star, at least two stars, at least three stars and up to four stars.

Cosmetically Acceptable Appearance

The topical sunscreen compositions for both preventing and repairing sun damage described herein can be formulated to achieve a cosmetically acceptable appearance. Without being bound by theory, it is thought that zinc oxide (ZnO) blocks ultraviolet (UV) radiation at wavelengths from 290 nm up to about 375 nm. In addition, zinc oxide has long been utilized for its antimicrobial and other properties. Despite these beneficial properties, use of zinc oxide has been limited primarily due to an undesirable whitening effect on the substrate to which a zinc oxide-containing product was applied. To the extent that zinc oxide was incorporated into dispersions for cosmetic and sunscreen formulations and products, formulators minimized ZnO levels and/or users applied the product sparingly or at levels lower than indicated to reduce or minimize whitening. In so doing, however, the photoprotective efficacy of the product was lessened. Similarly, such whitening was and is undesirable in photoprotective transparent coatings and transparent plastic films.

Without being bound by theory, whitening on a substrate (e.g., skin) after application of a photoprotective product containing dispersed ZnO powder is believed to be attributable to scattering of light from the particles in the backward direction (i.e., away from the substrate and toward the viewer). It is also thought that titanium dioxide can leave a whitish hue on the skin.

The main factors that affect the scattering of light from particles and hence whitening include the particle size and the refractive index of the particles relative to the media in which the particles are dispersed. In general, decreasing the size of the particles or the relative refractive index of the particles causes a decrease in scattering and whiteness of the product.

In several embodiments provided herein, the topical sunscreen compositions are relatively translucent or transparent so as to have a cosmetically acceptable appearance. In other words, the topical sunscreen compositions of some embodiments have a substantially translucent or transparent appearance on the skin and minimize the "whitening" effect on skin. In various embodiments, topical sunscreen compositions can comprise from about 1% to 25% by weight of particulate zinc oxide having an average particle size of from 0.05 microns to 0.5 microns. In some embodiments, topical sunscreen compositions can comprise from about 1% to 25% of particulate titanium dioxide having an average particle size of from 0.01 microns to 0.1 microns.

Super Antioxidants

Any of the embodiments drawn to topical compositions for repairing sun damaged skin and any of the embodiments drawn to topical sunscreen compositions for both preventing and repairing sun damage can further include one or more super antioxidants known in the art. Without being bound by theory, super antioxidants are considered to have high quantitative potency according to the Oxygen Radical Absorbance Capacity (ORAC) score developed by the USDA. For example, in various embodiments, a super antioxidant is an agent or composition that has an ORAC score of 8,000 or greater, 10,000 or greater, 12,000 or greater, 20,000 or greater, 30,000 or greater, or 50,000 or greater.

Any of a variety of known super antioxidants can be used in accordance with the teachings and compositions provided herein, and include, but are not limited to, green tea (ORAC score 11,000), coffeeberry (ORAC score 15,000), and ergothioneine (ORAC score 61,000). Additional known super antioxidants that can be used in embodiments provided herein include but are not limited to any of the following substances and/or their known active components: ground cloves (ORAC score 290,283), dried oregano spice (ORAC score 175,295), dried thyme spice (ORAC score 157,380), ground turmeric spice (ORAC score 127,068), dried rosemary spice (ORAC score 119,929), ground cinnamon spice (ORAC score 131,420), ground nutmeg (ORAC score 69,640), dried basil spice (ORAC score 61,063), ground ginger spice (ORAC score 39,041), black pepper spice (ORAC score 34,053), sage (ORAC score 32,004) dried wolfberry (ORAC score 30,300), mustard seed spice (ORAC score 29,257), marjoram (ORAC score 27,297), goji berries (ORAC score 25,300), chili powder (ORAC score 23,636), paprika (ORAC score 21,932), mangosteen (ORAC score 20,000), acai (ORAC score 18,400), black raspberry (ORAC score 16,400) black chokeberry (ORAC score 16,062), elderberry (ORAC score 14,697), peppermint (ORAC score 13,978), oregano (ORAC score 13,970), dark chocolate (ORAC score 13,120), and pomegranate (ORAC score 10,500). Further examples of known super antioxidants that can be used can be found in the USDA database for the ORAC scores of selected foods, which is herein incorporated by reference in its entirety; where the above-listed ORAC score differs from the ORAC score in the USDA database, the ORAC score in the USDA database will be considered the correct ORAC score.

Antioxidants

Any of the embodiments drawn to topical compositions for repairing sun damaged skin and any of the embodiments drawn to topical sunscreen compositions for both preventing and repairing sun damage can further include one or more antioxidants known in the art. Examples of suitable antioxidants include but are not limited to the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, ψ-lycopene) and derivatives thereof, chlorogenic acid and derivatives thereof, aurothioglucose, propylthiouracil and other thiols (e.g thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to [mu]mol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, iminodisuccinate, unsaturated fatty acids and derivatives thereof (e.g. γ-linolenic acid, linoleic acid, oleic acid), folic acid and derivatives thereof, furfurylidenesorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), and coniferyl benzoate of benzene resin, propyl gallate, ferulic acid, furfurylideneglucitol, carnosine, butylhydroxyltoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnSO4), selenium and derivatives thereof (e.g. selenomethionine), stilbenes and derivatives thereof (e.g. stilbene oxide, trans-stilbene oxide), carboxymethyl betaglucan, grape seed extract, green tea extract, tocopheryl acetate, Vitamin A related retinyl palmitate, and ergothioneine. Without being bound by theory, ergothioneine is an antioxidant that also blocks the activation of elastase and matrix metalloproteinases. If present, in various embodiments the amount of antioxidants may each or collectively range from about 0.001% to about 10% w/w, about 0.01% to about 8% w/w, or about 0.05% to about 5% w/w, or any amount or range in between the aforementioned ranges. In some embodiments, the amount of antioxidants can each or collectively be about 0.01% to about 0.5% w/w.

Vitamins

Any of the embodiments drawn to topical compositions for repairing sun damaged skin and any of the embodiments drawn to topical sunscreen compositions for both preventing and repairing sun damage can further include one or more vitamins known in the art, whether or not chosen for any antioxidant properties. Suitable vitamins may include but are not limited to ascorbic acid and derivatives thereof, such as ascorbyl palmitate and tetrahexyldecyl ascorbate; the B vitamins such as thiamine, riboflavin, pyridoxin, and the like; Vitamin A and the ester-based derivatives thereof, such as palmitate (e.g. retinyl palmitate), acetate, and the like, as well as Vitamin A in the form of beta carotene; Vitamin E and derivatives thereof, such as Vitamin E acetate, nicotinate, or other esters thereof; Vitamins D and K and Vitamin C. If present, in various embodiments the amount of vitamins may each range from about 0.001% to about 10% w/w, about 0.01% to about 8% w/w, about 0.05% to about 5% w/w. In some embodiments, the amount of vitamins can each or collectively be about 0.01% to about 0.5% w/w.

Surfactants

Any of the embodiments drawn to topical compositions for repairing sun damaged skin and any of the embodiments drawn to topical sunscreen compositions for both preventing and repairing sun damage can further include one or more surfactants known in the art.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the 'head') provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. Popular members of the anionic surfactant class are the alkyl sulfates and the soaps. Also contemplated as examples of anionic surfactants that can be used in several embodiments include stearic acid and sodium behenoyl actylate.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in "Pharmaceutical Dosage Forms," Marcel Dekker, Inc., New York, N.Y., 1988, p. 285). Preferably such surfactants are nonionic and may be in the form of silicones or organic nonionic surfactants.

Suitable silicone surfactants include but are not limited to polyorganosiloxane polymers that have amphiphilic properties, for example contain hydrophilic radicals and lipophilic radicals. These silicone surfactants may be liquids or solids at room temperature. Examples of silicone surfactants that can be used in various embodiments include, but are not limited to: dimethicone copolyols, alkyl dimethicone copolyols, and emulsifying silicone elastomers. Emulsifying silicone elastomers are elastomers that have one or more hydrophilic groups such as hydroxyl, oxyethylene, and the like bonded thereto so as to confer hydrophilic properties to the elastomer. Suitable organic nonionic surfactants may include alkoxylated alcohols or ethers formed by the reaction of an alcohol with a polyalkyleneoxide containing repeating units of alkylene oxide. Preferably, the alcohol is a fatty alcohol having 6 to 30 carbon atoms. Examples of organic nonionic surfactants that can be used in various embodiments include, but are not limited to: steareth 2-100, beheneth 5-30, ceteareth 2-100, ceteareth-25, ceteth 1-45, and the like, which are formed by polyethyleneoxide with the corresponding stearyl/behenyl/cetyl alcohol (wherein the number as used herein designates the number of repeating units of ethylene oxide in the polyethyleneoxide). Other alkoxylated alcohols include esters formed by reaction of polymeric alkylene glycols with glyceryl fatty acid, such as PEG glyceryl oleates, PEG glyceryl stearate; or PEG polyhydroxyalkanotes such as PEG dipolyhydroxystearate wherein the number of repeating ethylene glycol units ranges from 3 to 1000. Nonionic surfactants formed by the reaction of a carboxylic acid with an alkylene oxide or with a polymeric ether are also suitable examples. Monomeric, homopolymeric, or block copolymeric ethers, alkoxylated sorbitan, alkoxylated sorbitan derivatives can also be used as nonionic surfactants in various embodiments.

If present, in various embodiments the amount of surfactants may each or collectively range from about 0.01% to 5.0% w/w or about 0.5% to 3.0% w/w, or any amount or range in between the aforementioned ranges. In some embodiments, the amount of surfactant can each or collectively be about 0.1% to 3.0% w/w.

Emulsifying Agents and Stabilizers

Any of the embodiments drawn to topical compositions for repairing sun damaged skin and any of the embodiments drawn to topical sunscreen compositions for both preventing and repairing sun damage can further include one or more emulsifying agents and stabilizers known in the art.

Suitable emulsifying agents include but are not limited to Octyl Stearate, Lauryl PEG-9 Polydimethylsiloxyethyl Dimethicone, Lecithin, Arachidyl Alcohol, Behenyl Alcohol, Arachidyl Glucoside, Cetyl Alcohol, PEG-100 Stearate, Polysorbate 20, Polysorbate 80, Stearic Acid, Sodium Behenoyl Lactylate, Laureth-7, Ethylhexyl Palmitate, Caprylic/Capric Triglyceride, Oleth-3 Phosphate, Hydroxyethyl Acrylate/Sodium Acryloyldimethyl Taurate Copolymer, Polyisobutene, PEG-7 Trimethylolpropane Coconut Ether, Dimethicone/PEG-10/15 Crosspolymer, Lauryl PEG-9 Polymethylsiloxyethyl Dimethicone, Dimethicone/Vinyl Dimethicone Crosspolymer, and Octyl Stearate.

Penetration Enhancers

Any of the embodiments drawn to topical compositions for repairing sun damaged skin and any of the embodiments drawn to topical sunscreen compositions for both preventing and repairing sun damage can further include one or more penetration enhancers known in the art. Without being bound by theory, penetration enhancers can be included to enhance efficient delivery of DNA repair enzymes to the skin.

Penetration enhancers may be classified as belonging to one of five broad categories, i.e., surfactants, fatty acids, bile salts, chelating agents, and non-chelating non-surfactants (Lee et al., Crit. Rev. Ther. Drug Carrier Systems, 1991, p. 92). Each of the above mentioned classes of penetration enhancers can be used in the compositions provided herein and are described below in greater detail.

1) Surfactants

As discussed above, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Crit. Rev. Ther. Drug Carrier Systems, 1991, p. 92); and perfluorchemical emulsions, such as FC-43 Takahashi et al., J. Pharm. Pharmacol., 1988, 40:252).

2) Fatty Acids

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Crit. Rev. Ther. Drug Carrier Systems, 1991, p. 92; Muranishi, Crit. Rev. Ther. Drug Carrier Systems, 1990, 7:1; El Hariri et al., J. Pharm. Pharmacol., 1992, 44:651).

3) Bile Salts

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pages 934-935). Various natural bile salts, and their synthetic derivatives, act as penetration enhancers. Thus the term "bile salts" includes any of the naturally occurring components of bile as well as any of their synthetic derivatives. The bile salts of some embodiments include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7:1; Yamamoto et al., J. Pharm. Exp. Ther., 1992, 263:25; Yamashita et al., J. Pharm. Sci., 1990, 79:579).

4) Chelating Agents

Chelating agents, as used in connection with some embodiments, can be defined as compounds that remove metallic ions from solution by forming complexes therewith, with the result that absorption of oligonucleotides through the mucosa is enhanced. With regards to their use as penetration enhancers in some embodiments, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315). Chelating agents of some embodiments include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7:1; Buur et al., J. Control Rel., 1990, 14:43).

5) Non-Chelating Non-Surfactants

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, Critical Reviews in Therapeutic Drug Carrier Systems, 1990, 7:1). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39:621).

A penetration enhancer that can be included in many embodiments is comprised of two components—a hydrophobic component and a hydrophilic component. Desirably, the hydrophobic component comprises a polyether compound, such as an ethoxylated vegetable, nut, synthetic, or animal oil, which has the ability to reduce the surface tension of materials that are dissolved into it. Not wanting to be tied to any particular mechanism or mode of action and offered only to expand the knowledge in the field, it is contemplated that the attachment of poly(ethylene oxide) to the components of a particular oil occurs not on a particular functional group but rather the polyethylene oxide chains begin to grow from unsaturated C=C bonds and from the occasional glycerol unit. Because an ethoxylated oil, such as ethoxylated *macadamia* nut oil, is a mixture of various fatty acids, fatty alcohols, and fatty amines, the components of the oil may have varying amounts of ethoxylation. Accordingly, measurements of ethoxylation/molecule (e.g., 16 ethoxylations/molecule) are an average of the amount of ethoxylation present on the components of the oil rather than on any specific component itself.

Ethoxylated oils can be obtained or created from, for example, *macadamia* nut oil, meadowfoam, castor oil, jojoba oil, corn oil, sunflower oil, sesame oil, and emu oil. Many of these oils are commercially available from Floratech of Gilbert, Ariz. or other suppliers. Alternatively, ethoxylated oils can be prepared by reacting the oil with ethylene oxide. It is contemplated that ethoxylated fatty acids, ethoxylated fatty alcohols, and ethoxylated fatty amines, in particular ethoxylated fatty acids, ethoxylated fatty alcohols, and ethoxylated fatty amines that contain 12, 13, 14, 15, 16, 17, 18, or 19 ethoxylations are suitable penetration enhancers for use in the embodiments described herein. These ethoxylated oil components can be used individually as penetration enhancers or as supplements to other penetration enhancers (e.g., ethoxylated *macadamia* nut oil).

If present, in various embodiments the amount of penetration enhancers may each or collectively range from about 0.01% to 5.0% w/w or about 0.5% to 3.0% w/w, or any amount or range in between the aforementioned ranges. In some embodiments, the amount of penetration enhancers can each or collectively be about 0.1% to 3.0% w/w.

Ceramides

Any of the embodiments drawn to topical compositions for repairing sun damaged skin and any of the embodiments drawn to topical sunscreen compositions for both preventing and repairing sun damage can further include one or more ceramides known in the art. Ceramides are one of human skin components and have skin-moisturizing and protecting functions and skin-roughness-preventing and improving effects. Examples of suitable ceramides include but are not limited to long chain ceramides, glucosylceramides, galactosylceramides, diisopropylamine dichloro acetate, and gamma aminobutyric acid.

If present, in various embodiments the amount of ceramides may each range from about 0.001% to 0.5% w/w or about 0.01% to 0.05% w/w, or any amount or range in between the aforementioned ranges.

Collagen Stimulants

Any of the embodiments drawn to topical compositions for repairing sun damaged skin and any of the embodiments drawn to topical sunscreen compositions for both preventing and repairing sun damage can further include one or more collagen stimulants known in the art. Without being bound by theory, collagen stimulants are thought to restore collagen production, stimulate fibroblast cells in the skin, flush pigments in the skin, and/or strengthen the vascular network.

Examples of suitable collagen stimulants include but are not limited N-hydroxysuccinimide chrysin, matrikines such as palmitoyl oligopeptide and palmitoyl tetrapeptide-7, and caprooyl tetrapeptide-3, which is a peptide based on transforming growth factor (TFG-β).

If present, in various embodiments the amount of collagen stimulants may each or collectively range from about 0.001% to 0.5% w/w or about 0.01% to 0.05% w/w, or any amount or range in between the aforementioned ranges. In some embodiments, the aforementioned amounts and ranges of collagen stimulants is in addition to any metal peptide complex, if present.

Aqueous Adjuvants

Any of the embodiments drawn to topical compositions for repairing sun damaged skin and any of the embodiments drawn to topical sunscreen compositions for both preventing and repairing sun damage can further include one or more aqueous adjuvants known in the art. Several embodiments described herein comprise an aqueous adjuvant such as *Aloe Vera* juice or water or both. The term "Aloe" refers to the genus of South African plants of the Liliaceae family, of which the Aloe barbadensis plant is a species. Aloe is an intricate plant, which contains many biologically active substances. (Cohen, et al. in Wound Healing/Biochemical and Clinical Aspects, 1st ed. W B Saunders, Philadelphia (1992)). Over 300 species of Aloe are known, most of which are indigenous to Africa. Studies have shown that the biologically active substances are located in three separate sections of the Aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See e.g., Grindlay and Reynolds (1986) J. of Ethnopharmacology 16:117-151; Hart, et al. (1988) J. of Ethnopharmacology 23:61-71). As a result of these studies there have been numerous reports of Aloe compounds having diverse biological activities, including anti-tumor activity, anti-gastric ulcer, anti-diabetic, anti-tyrosinase activity, (See e.g., Yagi, et al. (1977) Z. Naturforsch. 32c:731-734), and antioxidant activity (International Application Ser. No. PCT/US95/07404).

Recent research has also shown that *Aloe Vera*, a term used to describe the extract obtained from processing the entire leaf, isolated from the *Aloe Vera* species of Aloe, can be used as a vehicle for delivering hydrocortisone, estradiol, and testosterone propionate. (See Davis, et al, JAPMA 81:1 (1991) and U.S. Pat. No. 5,708,038 to Davis)). As set forth in Davis (U.S. Pat. No. 5,708,308), one embodiment of "*Aloe Vera*" can be prepared by "whole-leaf processing" of the whole leaf of the Aloe barbadensis plant. Briefly, whole leaves obtained from the Aloe barbadensis plant are ground, filtered, treated with cellulase (optional) and activated carbon and lyophilized. The lyophilized powder is then reconstituted with water prior to use.

*Aloe Vera* can be obtained commercially through Aloe Laboratories, for example. In other embodiments, the *Aloe Vera* is made as follows. First, the leaves are manually harvested. Next, the leaves are washed with water and the thorns on both ends are cut. The leaves are then hand-filleted so as to extract the inner part of the leaf. The inner gel is passed through a grinder and separator to remove fiber from the gel. Then the gel is put into a pasteurizing tank where L-Ascorbic Acid (Vitamin C) and preservatives are added. The gel is pasteurized at 85.degree. C. for 30 minutes. After pasteurization, the gel is put into a holding tank for about one or two days, after which the gel is sent through a ½ micron filter. Finally, the gel is cooled down through a heat exchanger and stored in a steamed, sanitized and clean 55 gallon drum. The above described sources and manufacturing methods of *Aloe Vera* are given as examples and not intended to limit the scope of any embodiment. One of ordinary skill in the art will recognize that *Aloe Vera* is a well known term of art, and that

*Aloe Vera* is available from various sources and manufactured according to various methods.

Absolute *Aloe Vera* (100% pure) can also be obtained from commercial suppliers (Lily of the Desert, Irving, Tex.). *Aloe Vera* juice, prepared from gel fillet, has an approximate molecular weight of 200,000 to 1,400,000 daltons. Whole leaf *Aloe Vera* gel has a molecular weight of 200,000 to 3,000,000 depending on the purity of the preparation. In several embodiments, other extracts from a member of the Liliaceae family can be used (e.g., an extract from another Aloe species).

The amount of water in various embodiments, if any, depends on the amount of other reagents (e.g., extract, DNA repair enzyme, metal peptide complex, UV blocker, liposome, antioxidant, penetration enhancer, surfactants, other aqueous adjuvants or fillers, etc.). Although water is used as the sole aqueous adjuvant in some embodiments, several embodiments use enough water to make the total volume of a particular preparation of a topical composition such that the desired concentrations of reagents in the penetration enhancer, aqueous adjuvant, and delivered agent are achieved. Suitable forms of water are deionized, distilled, filtered or otherwise purified. Clearly, however, any form of water can be used as an aqueous adjuvant.

Moisturizing Agents

Any of the embodiments drawn to topical compositions for repairing sun damaged skin and any of the embodiments drawn to topical sunscreen compositions for both preventing and repairing sun damage can further include one or more moisturizing agents known in the art. Non-limiting examples of moisturizing agents that can be used in various embodiments include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe barbadensis extract, aloe barbadensis gel, *althea officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, sphingosines (e.g. caprooyl-phytosphingosine and caprooyl-sphingosine), butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, fructose, gelatin, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica* limonum) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquarternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

Also contemplated as examples of moisturizing agents are skin conditioning agents and emollients known in the art. Non-limiting examples of skin conditioning agents and emollients that can be used in various embodiments include hydrogenated polydecene, glyceryl stearate, caprylyl glycol, *triticum vulgare* (wheat) gluten extract, lecithin, *glycine soja* (soybean) seed extract, octyldodecyl neopentanoate, c12-15 alkyl benzoate, dimethicone, ethylhexylglycerin, *camellia oleifera* leaf extract, *vitis vinifera* (grape) seed extract, propylene glycol isoceteth-3 acetate, ethylhexyl stearate, *prunus armeniaca* (apricot) kernel oil, n-hydroxysuccinimide, palmitoyl oligopeptide, palmitoyl tetrapeptide-7, sodium hyaluronate, sodium carboxymethyl betaglucan, *ilex paraguariensis* (paraguay tea) leaf extract, *centilla asiatica* extract, *echinecea purpurea* extract, *saccharomyces lysate* extract, *oenothera biennis* (evening primrose) oil, beeswax, cholesterol, allantoin, tridecyl stearate, *persea gratissima* (avocado) oil, isopropyl palmitate, octyl stearate, ethyl hexyl isononanoate, cyclopentasiloxane, glycereth-26, panthenol, cyclopentasiloxane, *camellia sinensis* leaf extract, aloe barbadensis extract, cyclomethicone, isopropyl palmitate, *helianthus annuus* (sunflower) seed oil, squalane, hydrogenated castor oil, *rosmarinus officinalis* (rosemary) leaf extract, xanthophyll, and melanin.

If present, in various embodiments the amount of moisturizing agents may each or collectively range from about 0.01% to 20% w/w, about 0.1% to 10%, or about 0.5% to 5%, or any amount or range in between the aforementioned ranges.

Medicaments

Any of the embodiments drawn to topical compositions for repairing sun damaged skin and any of the embodiments drawn to topical sunscreen compositions for both preventing and repairing sun damage can further include one or more medicaments known in the art. Examples of medicaments include but are not limited to menthol, camphor, *eucalyptus*, salicylic acid, allantoin, benzocaine, derivatives of salicylic acid, phenol and pramoxine. In some embodiments petrolatum and/or dimethicone may also provide medicament benefits. The above list is not an exhaustive list of medicaments and those of skill in the art may consider the use of other medicaments.

Typically medicaments which are added for medicament purposes only will be added in amounts of less than about 3%. Amounts may vary depending on the potency of the medicament and the matrix in which the medicament is presented. If present, in various embodiments the amount of medicaments may each range from about 0.1% to 40% w/w, about 0.5% to 35% w/w, or about 1.0% to 30% w/w, or any amount or range in between the aforementioned ranges.

Skin Lightening Agents

Any of the embodiments drawn to topical compositions for repairing sun damaged skin and any of the embodiments drawn to topical sunscreen compositions for both preventing and repairing sun damage can further include one or more skin lightening agents known in the art. Examples of suitable skin lightening agents include but are not limited to kojic acid, arbutin, tranexamic acid, ascorbic acid and derivatives, e.g., magnesium ascorbyl phosphate or sodium ascorbyl phosphate or other salts of ascorbyl phosphate, ascorbyl glucoside, and the like. Other suitable skin lightening agents include undecylenoyl phenylalanine (Sepiwhite® from SEPPIC), aloesin, and Actiwhite® (Cognis). If present, in various embodiments the amount of skin lightening agents may each or collectively range from about 0.001% to 10% w/w, about 0.02% to 4.0% w/w, or from about 0.05% to 2.0% w/w, or any amount or range in between the aforementioned ranges.

Colorants

Any of the embodiments drawn to topical compositions for repairing sun damaged skin and any of the embodiments drawn to topical sunscreen compositions for both preventing and repairing sun damage can further include one or more colorants known in the art.

Examples of suitable colorants include but are not limited to natural colorants such as plant extracts, caramel, natural minerals, or carmine, synthesized and/or processed colorant materials such as iron oxides, synthetic dyes, organic compounds, and FDA certified colorants for use on the lips. The above list is not an exhaustive list of colorants and those of skill in the art may consider the use of other colorants. Formulations of colorants are commercially available. An example of a commercially available colorant contains caprylic/capric triglycerides (59.5%), titanium dioxide (39.6%), castor oil phosphate (0.5%) and triethoxycaprylylsilane (0.4%). Optionally in some embodiments it may be desirable to include a color enhancer such as, for example, a pearlescent material.

If present, in various embodiments the amount of colorants may each or collectively range from about 0.001% to 10% w/w, about 0.02% to 4.0% w/w, or from about 0.05% to 2.0% w/w, or any amount or range in between the aforementioned ranges. In some embodiments, the amount of colorants can be about 0.02% to about 0.2% w/w.

In several embodiments, one or more colorants and their amount(s) can be selected to provide a diversity of flesh tones. In various embodiments, topical compositions described herein can be used as a makeup foundation.

Fragrances

Any of the embodiments drawn to topical compositions for repairing sun damaged skin and any of the embodiments drawn to topical sunscreen compositions for both preventing and repairing sun damage can further include one or more fragrances known in the art.

Examples of fragrances include but are not limited to a fragrant odoriferous substance or a mixture of fragrant odoriferous substances including natural substances obtained by extraction of flowers, herbs, leaves, roots, barks, wood, blossoms or plants; artificial substances including mixtures of different natural oils or oil constituents; and synthetically produced substances. Some examples of perfume ingredients that are useful include hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-isopropylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; and undecalactone gamma.

Additional examples of perfume ingredients include but are not limited to orange oil; lemon oil; grapefruit oil; bergamot oil; clove oil; dodecalactone gamma; methyl-2-(2-pentyl-3-oxo-cyclopentyl) acetate; beta-naphthol methylether; methyl-beta-naphthylketone; coumarin; decylaldehyde; benzaldehyde; 4-tert-butylcyclohexyl acetate; alpha, alpha-dimethylphenethyl acetate; methylphenylcarbinyl acetate; Schiff's base of 4-(4-hydroxy-4-methylpentyl)-3-cyclohexene-1-carboxaldehyde and methyl anthranilate; cyclic ethylene glycol diester of tridecandioic acid; 3,7-dimethyl-2,6-octadiene-1-nitrile; ionone gamma methyl; ionone alpha; ionone beta; petitgrain; methyl cedrylone; 7-acetyl-1,2,3,4,5,6,7,8-octahydro-1,1,6,7-tetramethyl-naphthalene; ionone methyl; methyl-1,6,10-trimethyl-2,5,9-cyclododecatrien-1-yl ketone; 7-acetyl-1,1,3,4,4,6-hexamethyltetralin; 4-acetyl-6-tert-butyl-1,1-dimethyl indane; benzophenone; 6-acetyl-1,1,2,3,3,5-hexamethylindane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; ambroxane; dodecahydro-3a,6,6,9a-tetramethylnaphtho-2,1b furan; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; and condensation products of: hydroxycitronellal and methyl anthranilate; hydroxycitronellal and indol; phenyl acetaldehyde and indol; 4-(4-hydroxy-4-methyl pentyl)-3-cyclohexene-1-carboxaldehyde, and methyl anthranilate.

Additional non-limiting examples of perfume ingredients include geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionones; irones; cis-3-hexenol and esters thereof; indane musk fragrances; tetralin musk fragrances; isochroman musk fragrances; macrocyclic ketones; macrolactone musk fragrances; bisabolol; and ethylene brassylate.

If present, in various embodiments the amount of fragrances may each range from about 0.001% to 10% w/w, about 0.02% to 4.0% w/w, or from about 0.05% to 2.0% w/w, or any amount or range in between the aforementioned ranges. In some embodiments, the amount of colorants can be about 0.02% to about 0.5% w/w.

Anti-inflammatory, Stress Reducing and Soothing Supplements

Any of the embodiments drawn to topical compositions for repairing sun damaged skin and any of the embodiments drawn to topical sunscreen compositions for both preventing and repairing sun damage can further include one or more supplements known in the art for inhibiting inflammation, reducing stress, and/or soothing aggravated skin.

Examples of supplements for inhibiting inflammation, reducing stress, and/or soothing aggravated skin include but are not limited to extracts of various *Evodia* species of plants such as *Evodia rutaecarpia*, lysates and extracts of various *Saccharomyces* species of yeast such as *Saccharomyces cerevisiae*, and bisabolol.

If present, in various embodiments the amount of anti-inflammatory, stress reducing and soothing supplements may each range from about 0.01% to 10% w/w, about 0.1% to 5.0% w/w, or from about 0.5% to 2.5% w/w, or any amount or range in between the aforementioned ranges.

Forms of Topical Compositions

The ingredients as described hereinabove can be provided in cosmetic compositions that may be formulated into a cream, gel, lotion, oil, ointment, powder, stick, cake, paste, film, or other forms that can be topically applied. The resulting topical compositions of several embodiments may be in the form of a liquid, solid, semi-solid, dispersion, suspension, solution or emulsion, and it can be either aqueous-based or anhydrous.

Formulations of various embodiments can include a pharmaceutically acceptable carrier such as water, oils (including vegetable and mineral oils), cream bases, lotion bases, ointment bases, and the like. These bases include suspending agents, thickeners, penetration enhancers, and the like. Topical and transdermal formulations are well known to those in the art of cosmetics and topical pharmaceuticals and are described, for example, in Chapter 44 of "Remington: The Science and Practice of Pharmacy 20 th edition" Lippincott Williams & Wilkins, Philadelphia, Pa. Eds Gennaro A. R. et al, 2000, which is incorporated herein by reference.

Topical formulations may also include pharmaceutically acceptable vehicles. Additives for topical formulations are well-known in the art, and may be added to the topical composition, as long as they are pharmaceutically acceptable and not deleterious to the epithelial cells or their function. Further, the additives should not cause deterioration in the stability of the formulation, in particular, of the extract or DNA repair enzymes. For example, inert fillers, anti-irritants, tackifiers, excipients, fragrances, opacifiers, antioxidants, gelling agents, stabilizers, surfactants, emollients, coloring agents, preservatives, buffering agents, other permeation enhancers, and other conventional components of transdermal delivery devices as are known in the art and can be included in any of the embodiments described herein. Excipients generally are carriers, diluents and/or vehicles used in formulating drug compositions. Excipients are standard in the art and examples of excipients and their application can be found, for instance, in Katz, M. {Drug Design 4:93-148,1973).

EXAMPLES

Having generally described embodiments drawn to topical compositions for repairing sun damaged skin and embodiments drawn to topical sunscreen compositions for both preventing and repairing sun damage, a further understanding can be obtained by reference to certain specific examples which are provided herein for purposes of illustration only, and are not intended to be limiting.

Example 1

A topical formulation was prepared containing the following components:

| Active Ingredient | % W/W |
|---|---|
| Bis(Tripeptide-1) Copper Acetate INCI AKA Prezatide Copper Acetate Chemical Name: Glycyl-Histidyl-Lysine-Copper 2 to 1 complex | 0.2000 |
| Plankton Extract | 0.0100 |

| Other Ingredients - By Weight | Function |
|---|---|
| Water | Solvent |
| Homosalate | Sunscreen |
| Octocrylene | Sunscreen |
| Octisalate | Sunscreen |
| Avobenzone | Sunscreen |
| Isododecane | Solvent |
| Hydrogenated Polydecene | Skin Conditioning Agent |
| Glycerin | Humectant |
| Glyceryl Stearate | Skin Conditioning Agent |
| Arachidyl Alcohol | Emulsion Stabilizer |
| Behenyl Alcohol | Emulsion Stabilizer |
| Ingredients ≤ 1% W/W | |
| Dimethicone | Skin Conditioning Agent |
| Arachidyl Glucoside | Emulsifying Agent |
| Caprylyl Glycol | Skin Conditioning Agent |
| Xanthan Gum | Thickening Agent |
| Cetyl Alcohol | Emulsifying Agent |
| PEG-100 Stearate | Emulsifying Agent |
| *Prunus Armeniaca* (Apricot) Kernel Oil | Skin Conditioning Agent |
| Squalane | Antioxidant |
| *Triticum Vulgare* (Wheat) Gluten Extract | Skin Conditioning Agent |
| Ammonium Acrylate/Acrylamide Copolymer | Thickening Agent |
| Polyisobutene | Thickening Agent |
| Polysorbate 20 | Emulsifying Agent |
| Sodium Hydroxide | pH Adjusting Agent |
| Lecithin | Skin Conditioning Agent |
| Sodium Chloride | Thickening Agent |
| *Glycine Soja* (Soybean) Seed Extract | Skin Conditioning Agent |
| Phenoxyethanol | Preservative |
| Sorbic Acid | Preservative |

As an example, liposomes containing plankton extract can be obtained commercially from Barnet Products Corporation (Englewood Cliffs, N.J.). The above components were mixed together to yield a topical formulation.

Example 2

A topical formulation was prepared containing the following components:

| Active Ingredient | % W/W |
|---|---|
| Bis(Tripeptide-1) Copper Acetate INCI AKA Prezatide Copper Acetate Chemical Name: Glycyl-Histidyl-Lysine-Copper 2 to 1 complex | 0.2000 |
| *Micrococcus luteus* Extract | 0.0090 |

| Other Ingredients - By Weight | Function |
|---|---|
| Water | Solvent |
| Glyceryl Stearate | Skin Conditioning Agent |
| Stearic Acid | Emulsifying Agent |
| Cetyl Alcohol | Emulsifying Agent |
| Sodium Behenoyl Lactylate | Emulsifying Agent |
| Octyldodecyl Neopentanoate | Emollient |
| C12-15 Alkyl Benzoate | Emollient |
| Cyclopentasiloxane | Solvent |
| Dimethicone | Skin Conditioning Agent |
| Ingredients ≤ 1% W/W | |
| Cyclohexasiloxane | Solvent |
| Phenoxyethanol | Preservative |
| Caprylyl Glycol | Skin Conditioning Agent |

| | |
|---|---|
| Ethylhexylglycerin | Skin Conditioning Agent |
| Hexylene Glycol | Solvent |
| Hydroxyethylcellulose | Thickening Agent |
| Sodium Hyaluronate | Skin Conditioning Agent |
| Sodium Carboxymethyl Betaglucan | Viscosity Increasing Agent |
| Ceteareth-25 | Surfactant |
| Glycerin | Humectant |
| Behenic Acid | Surfactant |
| Cholesterol | Skin Conditioning Agent |
| Ceramide EOP | Skin Conditioning Agent |
| Ceramide EOS | Skin Conditioning Agent |
| Ceramide NP | Skin Conditioning Agent |
| Ceramide NS | Skin Conditioning Agent |
| Ceramide AP | Skin Conditioning Agent |
| Caprooyl-Phytosphingosine | Skin Conditioning Agent |
| Caprooyl-Sphingosine | Skin Conditioning Agent |
| Butylene Glycol | Solvent |
| *Camellia Oleifera* Leaf Extract | Skin Conditioning Agent |
| Propylene Glycol | Solvent |
| *Vitis Vinifera* (Grape) Seed Extract | Skin Conditioning Agent |
| Propylene Glycol Isoceteth-3 Acetate | Emollient |
| Ethylhexyl Stearate | Skin Conditioning Agent |
| Tocopheryl Acetate | Antioxidant |
| *Prunus Armeniaca* (Apricot) Kernel Oil | Skin Conditioning Agent |
| Squalane | Antioxidant |

As an example, liposomes containing *Micrococcus luteus* extract can be obtained commercially from Barnet Products Corporation (Englewood Cliffs, N.J.). The above components were mixed together to yield a topical formulation.

Example 3

A topical formulation was prepared containing the following components:

| Active Ingredient | % W/W |
|---|---|
| Bis(Tripeptide-1) Copper Acetate INCI AKA Prezatide Copper Acetate Chemical Name: Glycyl-Histidyl-Lysine-Copper 2 to 1 complex | 0.5000 |
| *Arabidopsis Thaliana* Extract | 0.0045 |

| Other Ingredients - By Weight | Function |
|---|---|
| Water | Solvent |
| Dimethicone | Skin Conditioning Agent |
| Cyclopentasiloxane | Solvent |
| Cyclohexasiloxane | Solvent |
| Polysorbate 20 | Thickening Agent |
| Poylacrylamide | Thickening Agent |
| Ingredients ≤ 1% W/W | |
| Ceteareth-25 | Surfactant |
| Glycerin | Humectant |
| Cetyl Alcohol | Emulsifying Agent |
| Behenic Acid | Surfactant |
| Cholesterol | Skin Conditioning Agent |
| Ceramide EOP | Skin Conditioning Agent |
| Ceramide EOS | Skin Conditioning Agent |
| Ceramide NP | Skin Conditioning Agent |
| Ceramide NS | Skin Conditioning Agent |
| Ceramide AP | Skin Conditioning Agent |
| Caprooyl-Phytosphingosine | Skin Conditioning Agent |
| Caprooyl-Sphingosine | Skin Conditioning Agent |
| C13-14 Isoparaffin | Solvent |
| Laureth-7 | Emulsifying Agent |
| Steareth-20 | Surfactant |
| N-Hydroxysuccinimide | Skin Conditioning Agent |
| Chrysin | Skin Conditioning Agent |
| Palmitoyl Oligopeptide | Skin Conditioning Agent |
| Palmitoyl Tetrapeptide-7 | Skin Conditioning Agent |
| Sodium Hyaluronate | Skin Conditioning Agent |
| Sodium Carboxymethyl Betaglucan | Skin Conditioning Agent |
| *Camellia Oleifera* (Green Tea) Leaf Extract | Skin Conditioning Agent |
| *Vitis Vinifera* (Grape) Seed Extract | Skin Conditioning Agent |
| Butylene Glycol | Solvent |

| | |
|---|---|
| *Ilex Paraguariensis* (Paraguay Tea) Leaf Extract | Skin Conditioning Agent |
| *Centilla Asiatica* Extract | Skin Conditioning Agent |
| *Echinecea Purpurea* Extract | Skin Conditioning Agent |
| *Saccharomyces* Lysate Extract | Skin Conditioning Agent |
| Lecithin | Skin Conditioning Agent |
| Microcrystalline Cellulose | Thickening Agent |
| Cellulose Gum | Thickening Agent |
| Ethylhexyl Palmitate | Emulsifying Agent |
| Caprylic/Capric Triglyceride | Emulsifying Agent |
| Tocopheryl Acetate | Antioxidant |
| *Oenothera Biennis* (Evening Primrose) Oil | Skin Conditioning Agent |
| Squalane | Antioxidant |
| Ubiquinone | Antioxidant |
| Phenoxyethanol | Preservative |
| Caprylyl Glycol | Skin Conditioning Agent |
| Ethylhexylglycerin | Skin Conditioning Agent |
| Hexylene Glycol | Solvent |

As an example, liposomes containing *Arabidopsis thaliana* extract can be obtained commercially from Barnet Products Corporation (Englewood Cliffs, N.J.). The above components were mixed together to yield a topical formulation.

Example 4

A topical formulation was prepared containing the following components:

| Active Ingredient | % W/W |
|---|---|
| Alanine/Histidine/Lysine Polypeptide Copper HCl INCI Alanyl-Histidyl-Lysine Copper Complex | 0.3200 |
| *Arabidopsis Thaliana* Extract | 0.0045 |

| | Function |
|---|---|
| Other Ingredients - By Weight | |
| Water (Aqua) | Solvent |
| Dimethicone | Skin Conditioning Agent |
| Cyclopentasiloxane | Solvent |
| Cyclohexasiloxane | Solvent |
| Polysorbate 20 | Thickening Agent |
| Polyacrylamide | Thickening Agent |
| Ingredients ≤ 1% W/W | |
| Acetyl Hexapeptide-3 [argireline] | Skin Conditioning Agent |
| C13-14 Isoparaffin | Solvent |
| Laureth-7 | Emulsifying Agent |
| Sodium Hyaluronate | Skin Conditioning Agent |
| Sodium Carboxymethyl Betaglucan | Skin Conditioning Agent |
| *Camellia Oleifera* (Green Tea) Leaf Extract | Skin Conditioning Agent |
| *Vitis Vinifera* (Grape) Seed Extract | Skin Conditioning Agent |
| Butylene Glycol | Solvent |
| *Ilex Paraguariensis* (Paraguay Tea) Leaf Extract | Skin Conditioning Agent |
| *Centella Asiatica* Extract | Skin Conditioning Agent |
| *Echinacea Purpurea* Extract | Skin Conditioning Agent |
| *Saccharomyces* Lysate Extract | Skin Conditioning Agent |
| Lecithin | Skin Conditioning Agent |
| Microcrystalline Cellulose | Thickening Agent |
| Cellulose Gum | Thickening Agent |
| Ethylhexyl Palmitate | Emulsifying Agent |
| Caprylic/Capric Triglyceride | Emulsifying Agent |
| Tocopheryl acetate | Antioxidant |
| *Oenethera Biennis* (Evening Primrose) Oil | Skin Conditioning Agent |
| Squalane | Antioxidant |
| Ubiquinone | Antioxidant |
| Phenoxyethanol | Preservative |
| Caprylyl Glycol | Skin Conditioning Agent |

| | |
|---|---|
| Ethylhexylglycerin | Skin Conditioning Agent |
| Hexylene Glycol | Solvent |

As an example, liposomes containing *Arabidopsis thaliana* extract can be obtained commercially from Barnet Products Corporation (Englewood Cliffs, N.J.). The above components were mixed together to yield a topical formulation.

Example 5

A topical formulation was prepared containing the following components:

| Active Ingredient | % W/W |
|---|---|
| Bis(Tripeptide-1) Copper Acetate INCI AKA Prezatide Copper Acetate Chemical Name: Glycyl-Histidyl-Lysine-Copper 2 to 1 complex | 0.1800 |
| *Arabidopsis Thaliana* Extract | 0.2500 |

| | Function |
|---|---|
| Other Ingredients - By Weight | |
| Water | Solvent |
| Caprylic/Capric Triglyceride | Emulsifying Agent |
| Butylene Glycol | Solvent |
| *Prunus Amygdalus Dulcis* (Sweet Almond) Oil | Solvent |
| *Simmondsia Chinensis* (Jojoba) Seed Oil | Solvent |
| Stearic Acid | Emulsifying Agent |
| PEG-100 Stearate | Surfactant |
| Glyceryl Stearate | Skin Conditioning Agent |
| *Ricinus Communis* (Castor) Seed Oil | Skin Conditioning Agent |
| Cetyl Alcohol | Emulsifying Agent |
| Ingredients ≤ 1% W/W | |
| Ceramide NP | Skin Conditioning Agent |
| Ceramlde NS | Skin Conditioning Agent |
| Ceramide EOS | Skin Conditioning Agent |
| Ceramide EOP | Skin Conditioning Agent |
| CeramideAP | Skin Conditioning Agent |
| Caprooyl Phytosphingosine | Skin Conditioning Agent |
| Caprooyl Sphingosine | Skin Conditioning Agent |
| Dimethicone | Skin Conditioning Agent |
| Polysorbate 80 | Emulsifying Agent |
| Lecithin | Skin Conditioning Agent |
| Beeswax | Skin Conditioning Agent |
| Ceteareth-25 | Surfactant |
| Glycerin | Humectant |
| Behenic Acid | Surfactant |
| Cholesterol | Skin Conditioning Agent |
| Sorbitan Stearate | Surfactant |
| *Vitis Vinifera* (Grape) Seed Extract | Skin Conditioning Agent |
| Magnesium Aluminum Silicate | Anticaking Agent |
| Allantoin | Skin Conditioning Agent |
| Xanthan Gum | Thickening Agent |
| Sodium Chloride | Thickening Agent |
| Triethanolamine | pH Adjusting Agent |
| Phenoxyethanol | Preservative |
| Caprylyl Glycol | Skin Conditioning Agent |
| Ethylhexylglycerin | Skin Conditioning Agent |
| Hexylene Glycol | Solvent |

As an example, liposomes containing *Arabidopsis thaliana* extract can be obtained commercially from Barnet Products Corporation (Englewood Cliffs, N.J.). The above components were mixed together to yield a topical formulation.

Example 6

A topical formulation was prepared containing the following components:

| Active Ingredient | % W/W |
|---|---|
| Bis(Tripeptide-1) Copper Acetate INCI AKA Prezatide Copper Acetate Chemical Name: Glycyl-Histidyl-Lysine-Copper 2 to 1 complex | 0.1000 |
| *Micrococcus luteus* Extract | 0.0045 |

| | Function |
|---|---|
| Other Ingredients - By Weight | |
| Water (Aqua) | Solvent |
| Glyceryl Stearate | Skin Conditioning Agent |
| Caprylic/Capric Triglyceride | Emulsifying Agent |
| C12-15 Alkyl Benzoate | Emollient |
| Stearic Acid | Surfactant |
| Cetyl Alcohol | Emulsifying Agent |
| Sodium Behenoyl Lactylate | Surfactant |
| Ingredients ≤ 1% W/W | |
| Tridecyl Stearate | Skin Conditioning Agent |
| Neopentyl Glycol Dicaprylate/Dicaprate | Thickening Agent |
| Tridecyl Trimellitate | Skin Conditioning Agent |
| Phenoxyethanol | Preservative |
| Caprylyl Glycol | Skin Conditioning Agent |
| Ethylhexylglycerin | Skin Conditioning Agent |
| Hexylene Glycol | Solvent |
| Hydroxyethylcellulose | Thickening Agent |
| Allantoin | Skin Conditioning Agent |
| Cyclopentasiloxane | Solvent |
| Cyclohexasiloxane | Solvent |
| Dimethicone | Skin Conditioning Agent |
| Tocopheryl Acetate | Antioxidant |
| Squalane | Antioxidant |
| *Persea Gratissima* (Avocado) Oil | Skin Conditioning Agent |
| Lecithin | Skin Conditioning Agent |
| Sodium Chloride | Thickening Agent |
| Fragrance (Parfum) | Fragrance |

As an example, liposomes containing *Micrococcus luteus* extract can be obtained commercially from Barnet Products Corporation (Englewood Cliffs, N.J.). The above components were mixed together to yield a topical formulation.

Example 7

A topical sunscreen formulation was prepared containing the following components:

| Active Ingredient | % W/W |
|---|---|
| Zinc Oxide | 7.50% |
| Octinoxate | 7.50% |
| Octisalate | 2.50% |
| *Micrococcus luteus* Extract | 1.0% |
| Plankton Extract | 1.0% |
| Ergothioneine | ≤1.0% |

| | Function |
|---|---|
| Other Ingredients - By Weight | |
| Purified Water | Hydrating agent |
| Isopropyl Palmitate | Aids spreading & moisture retention |
| Octyl Stearate | Aids spreading & moisture retention |
| Ethyl Hexyl Isononanoate | Aids spreading & moisture retention |
| Cyclopentasiloxane | Aids spreading & moisture retention |
| Cetearyl Glucoside | Emulsifier |
| Ingredients ≤ 1% W/W | |
| Lecithin | Emulsifier |
| Dimethicone | Aids spreading & moisture retention |
| Glycereth-26 | Aids spreading & moisture retention |
| Sodium Hyaluronate | Aids spreading & moisture retention |
| Panthenol | Aids spreading & moisture retention |

| | |
|---|---|
| Allantoin | Helps protect & heal damaged skin |
| Tocopheryl Acetate | Antioxidant: Vitamin E to prevent skin damage |
| Ascorbyl Palmitate | Antioxidant: Vitamin C to prevent skin damage |
| Oleth-3 Phosphate | Emulsifier |
| Hydroxyethyl Acrylate/Sodium Acryloyldimethyl Taurate Copolymer | Emulsifier |
| Polyisobutene | Emulsifier |
| PEG-7 Trimethylolpropane Coconut Ether | Emulsifier |
| Polyether-1 | Thickener |
| Phenoxyethanol | Preservative |
| Butylene Glycol | Solubilizer |
| Citric Acid | Adjusts pH |
| Iodopropynyl Butylcarbamate | Preservative |
| Triethoxycaprylylsilane | Coating on zinc oxide |

As an example, liposomes containing plankton extract and *Micrococcus luteus* extract can be obtained commercially from Barnet Products Corporation (Englewood Cliffs, N.J.). The above components were mixed together to yield a topical sunscreen formulation.

Example 8

A topical sunscreen formulation was prepared containing the following components:

| Active Ingredient | % W/W |
|---|---|
| Zinc Oxide | 8.00% |
| Octinoxate | 7.50% |
| Octisalate | 3.00% |
| *Micrococcus luteus* Extract | 1.0% |
| Plankton Extract | 1.0% |
| Ergothioneine | ≤1.0% |

| | Function |
|---|---|
| Other Ingredients - By Weight | |
| Purified Water USP | Carrying & hydrating agent |
| Cyclopentasiloxane | Light silicone for easy spreading |
| Ethyl Hexyl Isononanoate | Light ester for spreading |
| Ingredients ≤ 1% W/W | |
| Lecithin | Emulsifier |
| Dimethicone | Light ester for spreading |
| Dimethicone/PEG-10/15 Crosspolymer | Emulsifier component |
| Lauryl PEG-9 Polymethylsiloxyethyl Dimethicone | Emulsifier component |
| Dimethicone/Vinyl Dimethicone Crosspolymer | Emulsifier component |
| Retinyl Palmitate (Vitamin A) | Anti-Oxidant |
| Ascorbyl Palmitate (Vitamin C) | Anti-Oxidant |
| Sodium Chloride | Electrolyte |
| Phenoxyethanol | Preservative |
| Butylene Glycol | Solubilizer for preservative |
| Iodopropynyl Butylcarbamate | Preservative |
| Citric Acid | Adjusts pH |
| Sodium Hydroxide | Adjusts pH |

As an example, liposomes containing plankton extract and *Micrococcus luteus* extract can be obtained commercially from Barnet Products Corporation (Englewood Cliffs, N.J.). The above components were mixed together to yield a topical sunscreen formulation.

Example 9

A topical sunscreen formulation was prepared containing the following components:

| Active Ingredient | % W/W |
| --- | --- |
| Octinoxate | 6.50% |
| Titanium Dioxide | 3.50% |
| *Micrococcus luteus* Extract | 1.0% |
| Plankton Extract | 1.0% |
| Ergothioneine | ≤1.0% |

| Other Ingredients - By Weight | Function |
| --- | --- |
| *Camellia Sinensis* Leaf Extract | Skin Conditioning Agent |
| *Aloe Barbadensis* Extract | Skin Conditioning Agent |
| Octyl Stearate | Emulsifier |
| Cyclomethicone | Emollient |
| Isopropyl Palmitate | Emollient |
| *Helianthus Annuus* (Sunflower) Seed Oil | Skin Conditioning Agent |
| Lauryl PEG-9 Polydimethylsiloxyethyl Dimethicone | Emulsifier |
| Ingredients ≤ 1% W/W | |
| Hydrated Silica | Viscosity Increasing Agent |
| Microcrystalline Wax | Viscosity Increasing Agent |
| Squalane | Skin Conditioning Agent |
| Cetyl Dimethicone | Emollient |
| Hydrogenated Castor Oil | Skin Conditioning Agent |
| Sodium Chloride | Viscosity Increasing Agent |
| *Rosmarinus Officinalis* (Rosemary) Leaf Extract | Skin Conditioning Agent |
| Silica | Suspending Agent |
| Lecithin | Emulsifier |
| Xanthophyll | Skin Conditioning Agent |
| Phenoxyethanol | Preservative |
| Iodopropynyl Butylcarbamate | Preservative |
| Melanin | Skin Conditioning Agent |
| Caramel | Colorant |
| Iron Oxides | Colorant |

As an example, liposomes containing plankton extract and *Micrococcus luteus* extract can be obtained commercially from Barnet Products Corporation (Englewood Cliffs, N.J.). The above components were mixed together to yield a topical sunscreen formulation.

Example 10

Human female subjects presenting visible signs of damaged skin were given a treatment regimen as follows: the topical composition of Example 1 was administered on the face twice daily (a.m. & p.m.), the topical composition of Example 2 was administered on the face once daily (a.m.), and a topical composition containing *Arabidopsis Thaliana* Extract, plankton extract, and *Micrococcus luteus* extract in liposomes was administered twice daily (a.m. & p.m.) over a four-week period.

Multi-spectral imaging, a system which incorporates standard cross-polarized flash and UV photograph, was conducted on the subjects at the start and end of the four week treatment regimen. Using multi-spectral imaging, key visual information was recorded and measured, values of subsurface conditions were quantified, and fixed positioning and lighting were assigned to ensure accuracy of images between assessment and time points.

Figure 2:
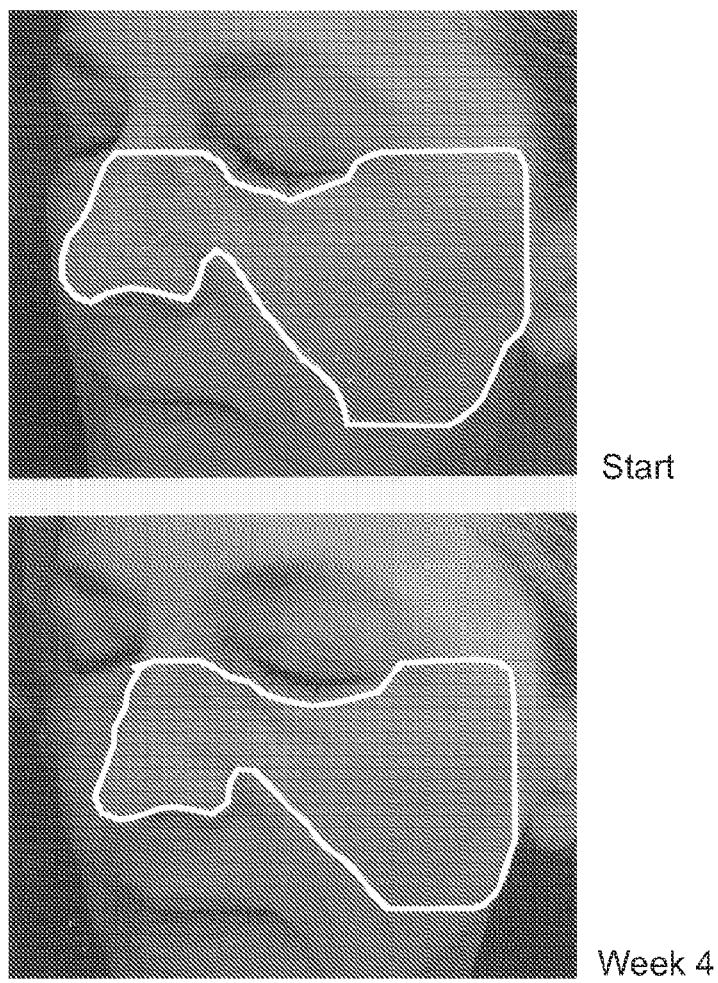
FIG. 2 is a panel of photographic images and a bar graph quantifying reduction in pores of a human female subject given a treatment regimen including various topical compositions described herein.
Figure 2:
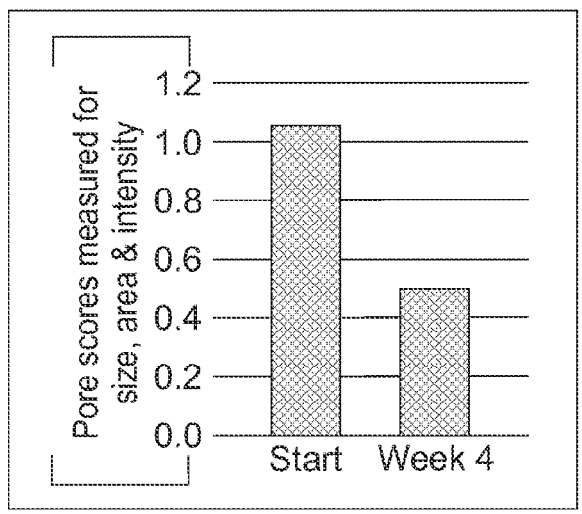
Figure 3:
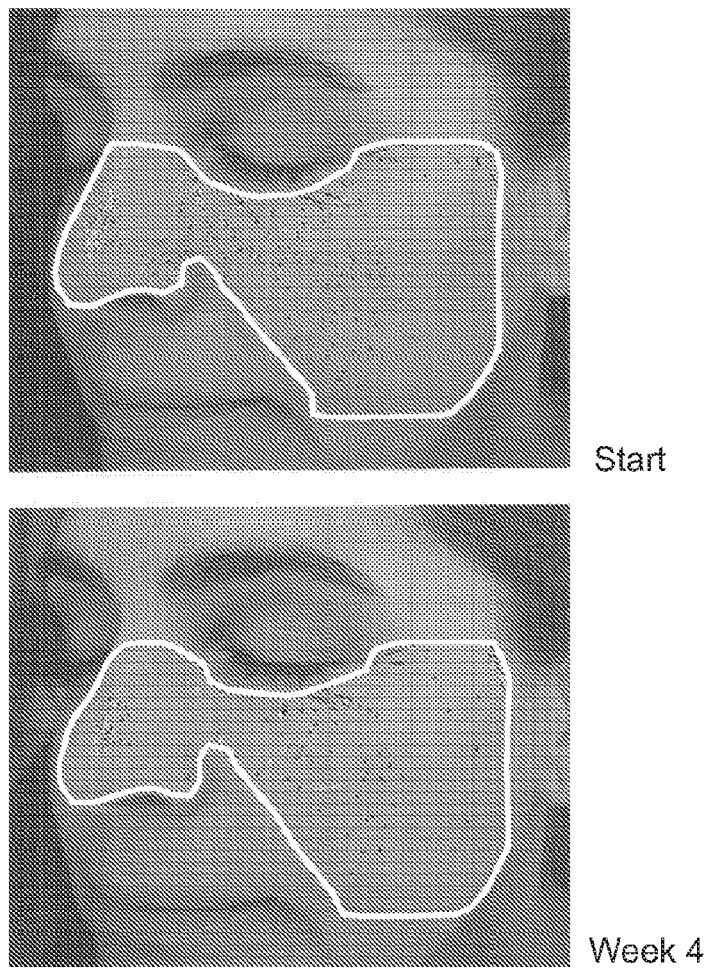
FIG. 3 is a panel of photographic images and a bar graph quantifying improvement in skin texture of a human female subject given a treatment regimen including various topical compositions described herein.
Figure 3:
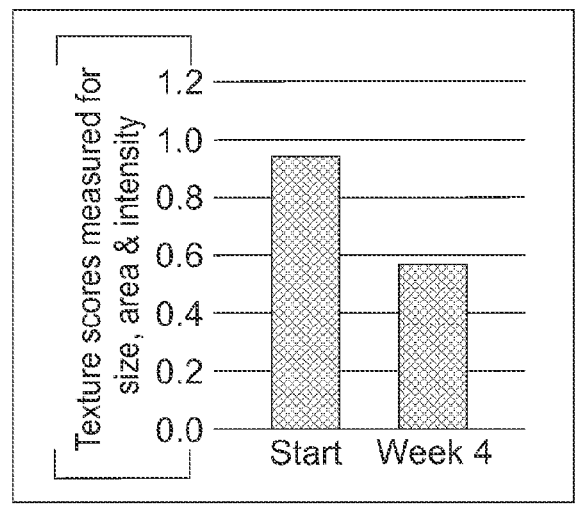

As shown in FIG. 1, the treatment regimen resulted in a >20% reduction in localized pigmentation of a representative subject. As shown in FIG. 2, the treatment regimen resulted in a >50% reduction in pores of a representative subject. As shown in FIG. 3, the treatment regimen resulted in a >40% improvement in skin texture of a representative subject.

These results show that the treatment regimen can be used to treat moderate photodamage categorized as Type II on the Glogau Photodamage Classification Scale, typically presenting with in-motion wrinkling, moderate discolorations, prominent pores, and early pigmentation changes.

Example 11

Human female subjects presenting visible signs of damaged skin were given a treatment regimen as follows: the topical composition of Example 3 was administered on the face twice daily (a.m. & p.m.) and the topical composition of Example 4 was administered on the face twice daily (a.m. & p.m.) over an eight-week period.

Multi-spectral imaging, a system which incorporates standard cross-polarized flash and UV photograph, was conducted on the subjects at the start and end of the eight week treatment regimen. Using multi-spectral imaging, key visual information was recorded and measured, values of subsurface conditions were quantified, and fixed positioning and lighting were assigned to ensure accuracy of images between assessment and time points.

Figure 4:
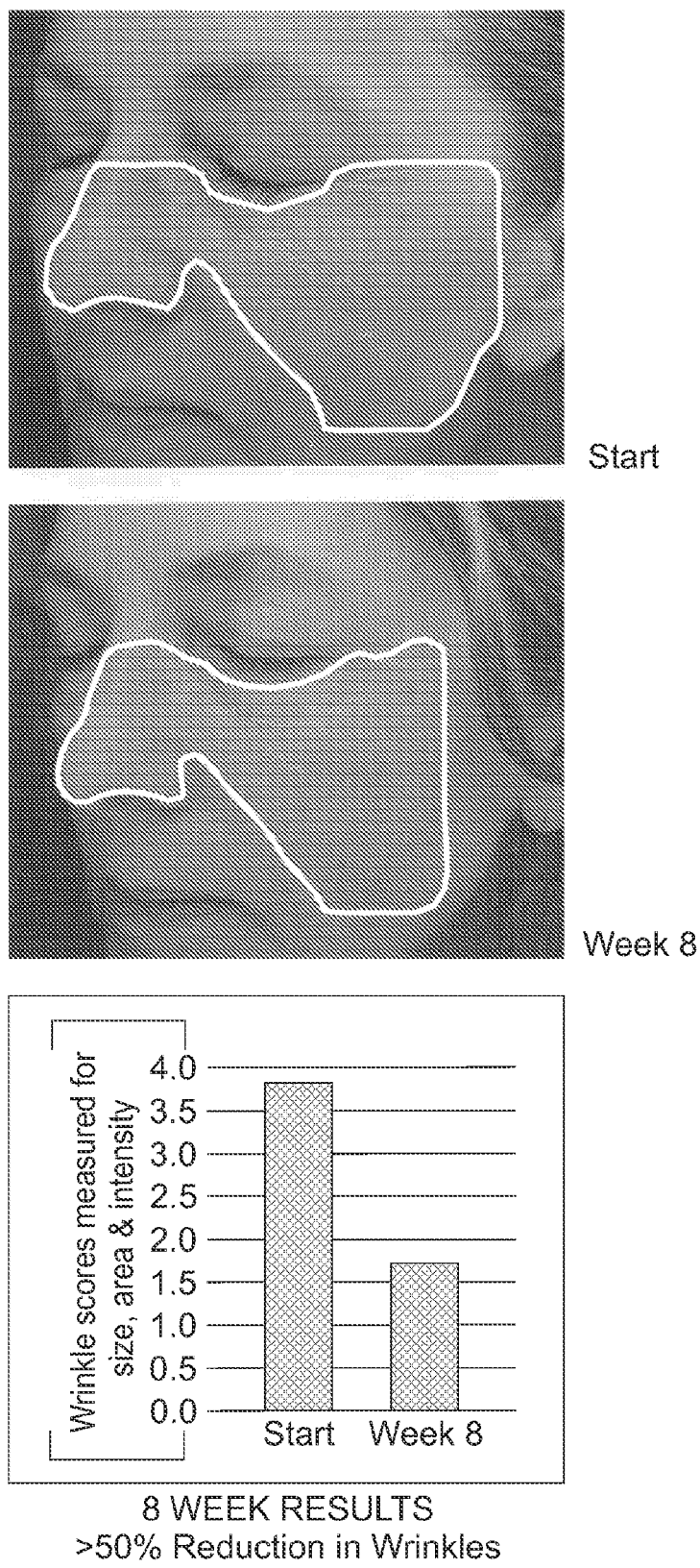
FIG. 4 is a panel of photographic images and a bar graph quantifying reduction in wrinkles of a human female subject given a treatment regimen including various topical compositions described herein.
Figure 5:
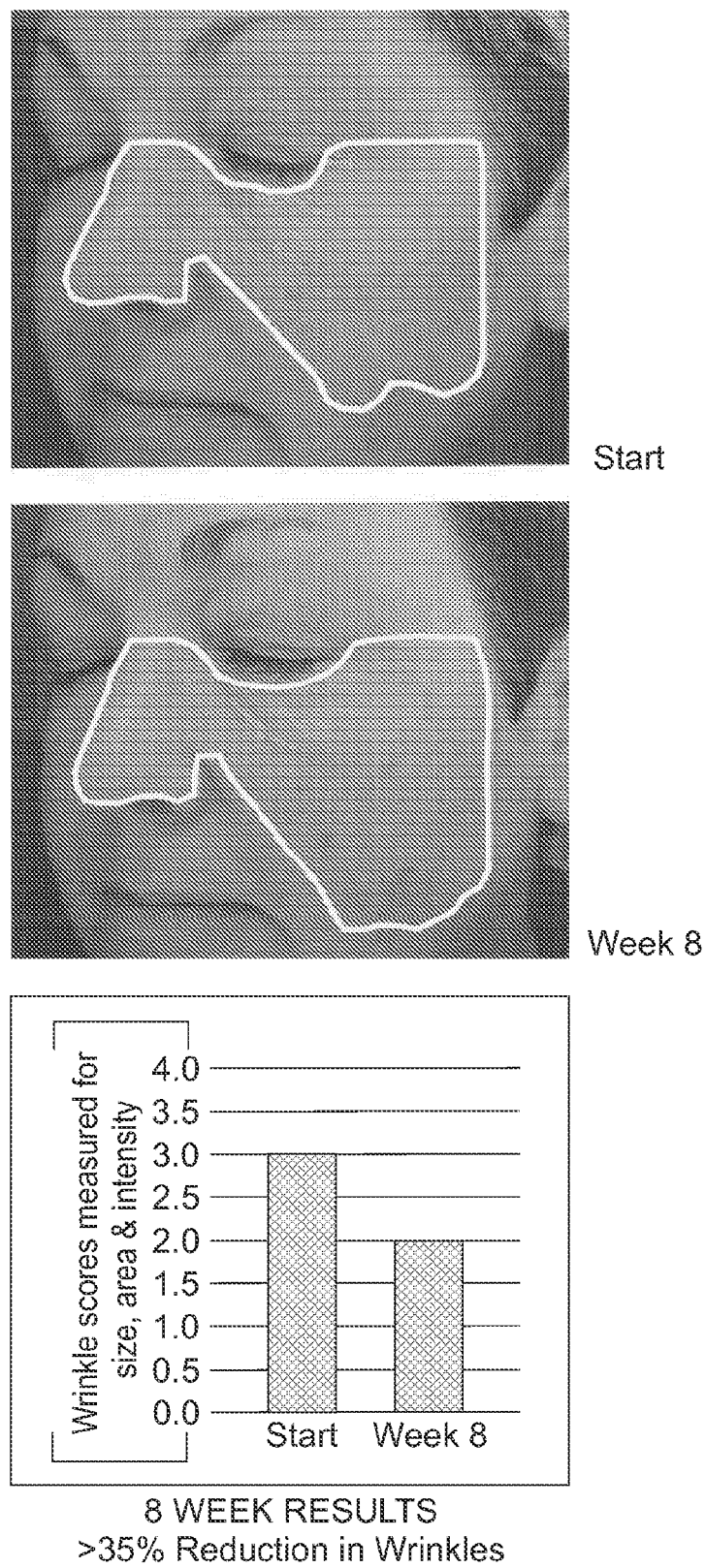
FIG. 5 is a panel of photographic images and a bar graph quantifying reduction in wrinkles of a human female subject given a treatment regimen including various topical compositions described herein.

As shown in FIG. 4, the treatment regimen resulted in a >50% reduction of wrinkles in a representative subject. As shown in FIG. 5, the treatment regimen resulted in a >35% reduction of wrinkles in a representative subject.

These results show that the treatment regimen can be used to treat periorbital aging categorized as Types I, II, and III on the Glogau Photodamage Classification Scale, typically presenting with crow's feet wrinkling, under-eye discoloration, and puffiness.

Example 12

Human female subjects presenting visible signs of damaged skin were given a treatment regimen as follows: the topical composition of Example 3 was administered on one side of the face twice daily (a.m. & p.m.) and the topical composition of Example 4 was administered on the same side of the face twice daily (a.m. & p.m.) over an eight-week period. The subjects were also given a placebo on the other side of the face over the eight-week period.

Multi-spectral imaging, a system which incorporates standard cross-polarized flash and UV photograph, was conducted on the subjects at the start and end of the eight week treatment regimen. Using multi-spectral imaging, key visual information was recorded and measured, values of subsurface conditions were quantified, and fixed positioning and lighting were assigned to ensure accuracy of images between assessment and time points.

Figure 6:
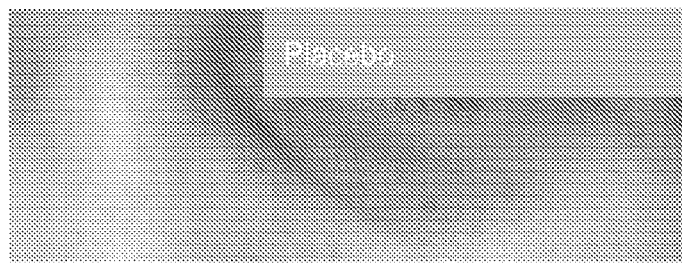
FIG. 6 is a panel of photographic images showing reduction in the intensity of dark, under-eye circles of a human female subject given a treatment regimen including various topical compositions described herein.
Figure 6:
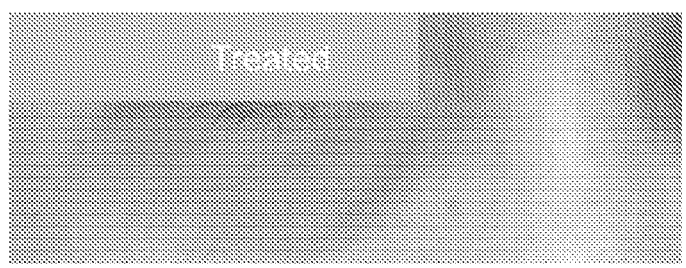

As shown in FIG. 6, the treatment regimen reduced the intensity of dark, under-eye circles in a representative subject. Furthermore, the treatment regimen reduced the intensity of dark, under-eye circles in over 60% of subjects by as much as 45%.

These results show that the treatment regimen can be used to treat periorbital aging categorized as Types I, II, and III on the Glogau Photodamage Classification Scale, typically presenting with crow's feet wrinkling, under-eye discoloration, and puffiness.

What is claimed is:

1. A topical sunscreen composition for repairing and reducing the incidence of sun damaged skin comprising:
   one or more DNA repair enzymes selected from the group consisting of: photolyase from Anacystis nidulans, UV endonuclease from Micrococcus luteus, and OGG1 from *Arabidopsis thaliana;*
   liposomes containing said one or more DNA repair enzymes; a peptone or synthesized peptide comprising a metal atom binding site; a metal atom bound to said metal binding site;
   wherein the liposomes comprise phospholipids, oleic acid, and cholesterol
   wherein the liposomes are about 200 nm in diameter; and a topically suitable carrier
   wherein the one or more enzymes are present in a cell extract.

2. The topical composition of claim 1, wherein the metal binding site comprises a nitrogen atom from at least two amino acids selected from Gly, Ala, Arg, His, and Lys.

3. The topical composition of claim 1, wherein the peptide consists of 3 amino acids
   wherein the 3 amino acids have the sequence Gly-His-Lys.

4. The topical composition of claim 1, wherein the peptide consists of 3 amino acids,
   wherein the 3 amino acids have the sequence Ala-His-Lys.

5. The topical composition of claim 1, wherein the metal atom is copper (II), cadmium (II), tin (II), cobalt (II), iron (II), or manganese (II).

* * * * *